United States Patent [19]

Young et al.

[11] Patent Number: 5,147,345
[45] Date of Patent: Sep. 15, 1992

[54] HIGH EFFICIENCY ABSORBENT ARTICLES FOR INCONTINENCE MANAGEMENT

[75] Inventors: Gerald A. Young, Cincinnati; Gary D. LaVon, Harrison; Gregory W. Taylor, Springdale, all of Ohio

[73] Assignee: The Procter & Gamble Company, Cincinnati, Ohio

[21] Appl. No.: 743,950

[22] Filed: Aug. 12, 1991

[51] Int. Cl.$^5$ .................. B32B 27/00; B32B 3/26; A61F 13/15; A61F 13/20
[52] U.S. Cl. .................. 604/378; 604/358; 604/367; 604/369; 604/374; 604/384; 428/286; 428/315.9
[58] Field of Search ............ 604/365, 367, 369, 374, 604/375, 378, 384, 358; 428/286, 315.9

[56] References Cited

U.S. PATENT DOCUMENTS

| | | | |
|---|---|---|---|
| 3,255,127 | 6/1966 | von Bonin | 260/2.5 |
| 3,431,911 | 3/1969 | Meisel | 128/287 |
| 3,563,243 | 2/1971 | Lindquist | 128/287 |
| 3,734,867 | 5/1973 | Will | 260/2.5 R |
| 3,763,056 | 10/1973 | Will | 260/2.5 L |
| 4,102,340 | 7/1978 | Mesek et al. | 128/287 |
| 4,394,930 | 7/1983 | Korpman | 220/444 |
| 4,473,611 | 9/1984 | Haq | 428/198 |
| 4,522,953 | 6/1985 | Barby et al. | 521/64 |
| 4,554,297 | 11/1985 | Dabi | 521/178 |
| 4,603,069 | 7/1986 | Haq et al. | 428/76 |
| 4,606,958 | 8/1986 | Haq et al. | 428/68 |
| 4,611,014 | 9/1986 | Jomes et al. | 521/146 |
| 4,612,334 | 9/1986 | Jones et al. | 521/146 |
| 4,636,209 | 1/1987 | Lassen | 604/378 |
| 4,659,564 | 4/1987 | Cox et al. | 424/65 |
| 4,668,709 | 5/1987 | Jones et al. | 521/146 |
| 4,673,402 | 6/1987 | Weisman et al. | 604/368 |
| 4,699,619 | 10/1987 | Bernardin | 604/378 |
| 4,699,620 | 10/1987 | Bernardin | 604/385 A |

(List continued on next page.)

FOREIGN PATENT DOCUMENTS

| | | |
|---|---|---|
| 2017570 | 11/1990 | Canada . |
| 0299122 | 1/1989 | European Pat. Off. . |
| 0299762 | 1/1989 | European Pat. Off. . |
| 0397110 | 11/1990 | European Pat. Off. . |
| 0399564 | 11/1990 | European Pat. Off. . |
| 0410480 | 1/1991 | European Pat. Off. . |
| 0427317 | 5/1991 | European Pat. Off. . |
| 0440472 | 8/1991 | European Pat. Off. . |
| 2-239863 | 9/1990 | Japan . |
| 2-289608 | 11/1990 | Japan . |
| 3-49759 | 3/1991 | Japan . |
| 2078527 | 1/1982 | United Kingdom . |

OTHER PUBLICATIONS

The Canadian Pulp and Paper Association, "The Determination of Freeness", Oct. 1981, pp. 1-6.
The Technical Association of the Pulp and Paper Association, "Tappi Test Methods, Volume One", 1989, pp. 1-6.

(List continued on next page.)

*Primary Examiner*—Randall L. Green
*Assistant Examiner*—A. P. Zuttarelli

[57] ABSTRACT

Disclosed are absorbent articles, such as diapers, for the management of incontinence. Such articles utilize in their absorbent cores a fluid acquisition/distribution component and a fluid storage/redistribution component maintained in fluid communication with the acquisition/distribution component. The fluid acquisition/distribution component can be any porous hydrophilic, e.g., fibrous or foam-based, material which will provide an initial Fluid Acquisition Rate of at least 2 mL of synthetic urine per second and will also preferably provide a 30-minute Vertical Wicking Height of at least 2 cm. The fluid storage/redistribution component comprises a hydrophilic, flexible, open-celled polymeric foam having a free absorbent capacity of at least about 12 mL of synthetic urine per gram of dry foam and an absorbent capacity under a 5.1 kPa confining pressure which is at least 5% of this free capacity. Preferred fluid acquisition/distribution component materials comprise chemically stiffened, twisted, curled cellulosic fibers. Preferred fluid storage/redistribution component materials comprise absorbent foams prepared by polymerizing a high internal phase emulsion (HIPE).

21 Claims, 4 Drawing Sheets

U.S. PATENT DOCUMENTS

| | | | |
|---|---|---|---|
| 4,788,225 | 11/1988 | Edwards et al. | 521/147 |
| 4,797,310 | 1/1989 | Barby et al. | 428/71 |
| 4,798,603 | 1/1989 | Meyer et al. | 604/378 |
| 4,822,453 | 4/1989 | Dean et al. | 162/157.6 |
| 4,839,395 | 6/1989 | Masamizu et al. | 521/56 |
| 4,888,093 | 12/1989 | Dean et al. | 162/157.6 |
| 4,888,231 | 12/1989 | Angstadt | 428/213 |
| 4,889,595 | 12/1989 | Herron et al. | 162/157.6 |
| 4,889,596 | 12/1989 | Schoggen et al. | 162/157.6 |
| 4,889,597 | 12/1989 | Bourbon et al. | 162/157.6 |
| 4,898,642 | 2/1990 | Moore et al. | 162/157.6 |
| 4,935,022 | 6/1990 | Lash et al. | 604/368 |
| 4,957,810 | 9/1990 | Eleouet et al. | 428/306.6 |
| 4,985,467 | 1/1991 | Kelly et al. | 521/52 |
| 4,988,344 | 1/1991 | Reising et al. | 604/368 |
| 4,988,345 | 1/1991 | Reising | 604/368 |
| 4,994,037 | 2/1991 | Bernardin | 604/368 |
| 5,009,650 | 4/1991 | Bernardin | 604/378 |

OTHER PUBLICATIONS

Aubert et al.,—"Low-Density, Microcellular Polystyrene Foams", *Polymer*, 1985, vol. 26, Dec.

Weber et al.,—"New Melamine-Based Elastic Foam," *Kunststoffe* 75 (1985) 11, pp. 843–848.

Young et al.,—"Preparation of Multishell ICF Target Plastic Foam Cushion Materials by Thermally Induced Phase Inversion Processes," *J. Vol. Sci. Technol.*, 20(4) Apr., 1982, pp. 1094–1097.

Lissant et al.,—"Structure of High-Internal-Phase-Ratio Emulsions," *Journal of Colloid and Interface Science*, vol. 47, No. 2, May, 1974.

Lissant et al.,—"A Study of Medium and High Internal Phase Ratio Water/Polymer Emulsions," *Journal of Colloid and Interface Science*, vol. 42, No. 1, Jan, 1973.

Lissant—"The Geometry of High-Internal Phase-Ratio Emulsions," *Journal of Colloid and Interface Science*, vol. 22, 462–468 (1966).

LeMay—"Mechanical Structure-Property Relationships of Microcellular, Low Density Foams," *Mat. Res. Soc. Symp. Proc.*, vol. 207, 1991, (pp. 21–26).

Gibson/Ashby—Cellular Solids, Structure and Properties, Pergamon Press, 1988.

0 10u

HIGH EFFICIENCY ABSORBENT ARTICLES FOR INCONTINENCE MANAGEMENT

This invention relates to absorbent articles which are to be worn by incontinent individuals in order to acquire and store aqueous body fluids discharged by the wearer of the absorbent article. Absorbent articles of this type include infant disposable diapers, diaper inserts, adult incontinence pads and briefs and the like which are required to handle relatively large amounts of discharged body fluids.

Incontinence management articles such as non-cloth, disposable diapers have traditionally utilized absorbent structures which comprise entangled masses of fibers, i.e., non-woven fibrous webs, to provide the requisite absorbency performance. These structures can imbibe liquids, such as discharged body fluids, both by absorption wherein fluid is taken up by the fiber material itself and by wicking wherein fluid distributed through and stored in the capillary interstices between fibers.

One objective in developing improved incontinence management articles over the years has been to increase both the total absorbent capacity of such articles as well as the tenacity with which such articles hold their absorbed load of body fluid. One means for realizing this objective and for improving the absorbency characteristics of fibrous web structures has been to incorporate therein so-called superabsorbent polymers which imbibe absorbed fluid to thereby form a swollen hydrogel material. The resulting hydrogel serves to retain fluid such as discharged body liquids within the structure. An absorbent structure of this type wherein hydrogel-forming materials in particulate form are incorporated into fibrous webs is disclosed in Weisman and Goldman; U.S. Pat. No. 4,610,678; Issued Sep. 9, 1986.

Another means for realizing incontinence management articles of improved absorbency characteristics has been to utilize in the absorbent cores of such articles various types of polymeric foam materials as the fluid-absorbing element. For example, Lindquist; U.S. Pat. No. 3,563,243; Issued Feb. 16, 1971 discloses an absorbent pad for diapers and the like wherein the primary absorbent therein is a hydrophilic foam sheet formed from hydrophilic polymers. Also, Dabi; U.S. Pat. No. 4,554,297; Issued Nov. 19, 1985 discloses body fluid absorbing cellular polymers which can be used in diapers or catamenial products.

While both fiber/superabsorbent-based and polymeric foam-based absorbent structures can provide improved absorbency characteristics, structures of both types can present problems in transporting or distributing absorbed fluid from one region or zone of the absorbent structure to another. This can be troublesome in articles for incontinence management wherein body fluid to be absorbed is frequently discharged in discrete gushes over the time period that the article is worn. Each gush of fluid discharged in this manner will generally encounter the absorbent structure at the same place or area. Thus, absorbency of the overall structure can be diminished unless a mechanism is provided to efficiently move fluid within the structure to other unused or relatively dry parts of the absorbent structure.

A variety of absorbent structure configurations have been developed to improve the distribution of absorbed fluid throughout the absorbent structure or absorbent material used therein. For example, Weisman/Houghton/Gellert; U.S. Pat. No. 4,673,402; Issued Jun. 16, 1987 discloses absorbent articles having a dual layer absorbent core configuration. In such a configuration, a structure comprising a primary "upper" absorbent layer is positioned over a "lower" insert absorbent layer that serves to drain absorbed fluid from the upper layer absorbent structure.

Another absorbent structure configuration for absorbent articles such as diapers designed to provide improved fluid handling performance is described in Alemany/Berg; U.S. Pat. No. 4,834,735; Issued May 30, 1989. This patent discloses articles with an absorbent member having a relatively low density, relatively low basis weight fluid acquisition zone surrounded by a fluid storage zone. These zones of the absorbent member are positioned toward the front of the absorbent article so as to most efficiently and effectively acquire, distribute, and store discharged body fluid.

Still other absorbent articles designed for the rapid acquiring and storing of discharged body fluid are those described in Reising; U.S. Pat. No. 4,988,345 and Reising/Bergman/Clear/Guinn/Gomez-Santiago; U.S. Pat. No. 4,988,344; both Issued Jan. 29, 1991. These patents both disclose absorbent articles such as diapers having multiple layered absorbent cores. These absorbent cores contain fluid storage layers into which discharged body fluids are directed by fluid acquisition apertures or fluid acquisition zones in other layers of the cores.

Notwithstanding the existence of the products described in the foregoing patents, there is a continuing need to identify still additional preferred configurations for absorbent articles which permit more effective and efficient use of the absorbent materials and structures used therein. Articles which allow more complete utilization of their absorbent material via improved fluid transport and distribution characteristics will be articles which can employ only minimal amounts of such absorbent material. These articles are in turn more cost effective and can deliver benefits of less bulk, better fit and greater comfort for the wearer of the articles. It is therefore an object of the present invention to provide such absorbent articles having improved efficiency in handling body fluids discharged into them and greater effective utilization of the absorbent materials from which they are made.

SUMMARY OF THE INVENTION

The present invention relates to absorbent articles useful for absorbing aqueous body fluids discharged by incontinent individuals who wear the articles. Such absorbent articles comprise a relatively liquid impervious backing sheet, a relatively liquid-pervious topsheet and an absorbent core positioned between the backing sheet and the topsheet. The absorbent core itself comprises a fluid acquisition/distribution component positioned to receive discharged body fluids passing through the article topsheet and a fluid storage/redistribution component maintained in fluid communication with the fluid acquisition/distribution component.

The fluid acquisition/distribution component of the absorbent core comprises a porous hydrophilic absorbent structure which exhibits an initial Fluid Acquisition Rate of at least about 2.0 ml of synthetic urine per second. The porous hydrophilic absorbent structure of the acquisition/distribution component will also preferably exhibit a 30-minute Vertical Wicking Height of at least about 2 cm. The fluid storage/redistribution component of the absorbent core comprises a polymeric foam material in the form of a hydrophilic, flexible, open-celled structure. Such a foam structure has a free absorbent capacity at 37° C. of at least about 12 ml of synthetic urine per gram of dry foam material. This foam also has an absorbent capacity for synthetic urine, under a confining pressure of 5.1 kPa maintained for 15 minutes at 37° C., which is at least about 5% of the free absorbent capacity of the foam.

In a preferred absorbent core configuration, the fluid acquisition/distribution component comprises a fiber-based or foam-based "upper" layer which overlies a subjacent foam-based fluid storage/redistribution "lower" layer. A preferred material for use in fashioning the upper fluid acquisition/distribution layer in such a preferred absorbent core configuration is a nonwoven fibrous web comprising from about 50% to 100% by weight of chemically stiffened, twisted, curled cellulosic fibers and up to about 50% of a binding agent for these fibers. The fibrous web formed from such materials will preferably have certain wet and dry density and basis weight characteristics.

Preferred absorbent foam materials for use in or as the lower fluid storage/redistribution layer of the preferred absorbent core configuration herein comprise foams which can be prepared by polymerizing a specific type of water-in-oil emulsion having a relatively smaller amount of an oil phase and a relatively greater amount of a water phase. This type of polymerizable emulsion in general is known in the art as a high internal phase emulsion or "HIPE". Preferred HIPE based foams for use in this invention are those which have certain pore volume, capillary suction specific surface area, and resistance to compression deflection characteristics.

DETAILED DESCRIPTION OF THE INVENTION

Figure 1:
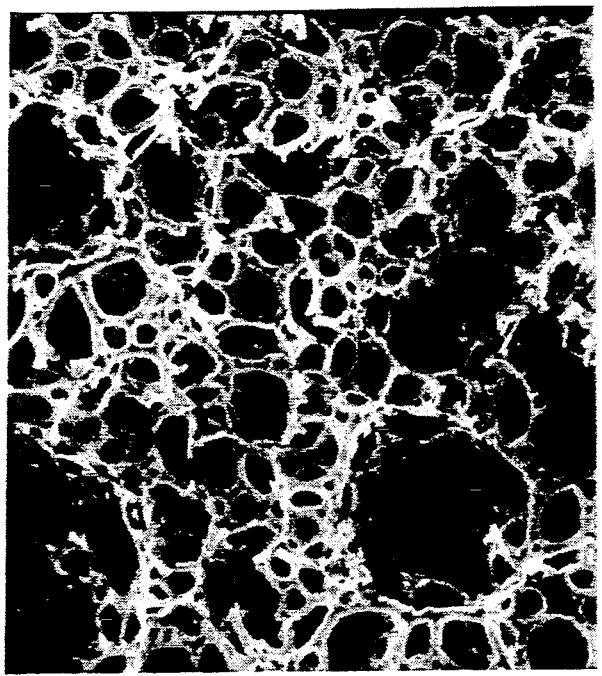
FIG. 1 of the drawings is a photomicrograph of the interstices of an absorbent HIPE foam material of the type preferably employed in the fluid storage/redistribution component of the absorbent core in the articles herein.

The absorbent articles of the present invention can be manufactured in the configuration of wearable disposable products which are capable of absorbing significant quantities of aqueous body waste fluids (i.e., liquids) such as urine and feces. Thus such articles, for example, may be prepared in the form of disposable diapers, diaper inserts, adult incontinence briefs, adult incontinence pads and the like, which are used by incontinent individuals.

ABSORBENT ARTICLE ELEMENTS

The absorbent articles herein generally comprise three basic structural components. One such component is an elongated, liquid impervious backing sheet. On top of this backing sheet is placed an absorbent core which itself comprises two or more distinct components or layers. On top of this absorbent core is placed a water pervious topsheet. The topsheet is the element of the article which is placed closest or next to the skin of the wearer.

Especially preferred absorbent articles of this invention are disposable diapers. Articles in the form of disposable diapers are fully described in Duncan and Baker, U.S. Pat. No. Re 26,151, Issued Jan. 31, 1967; Duncan, U.S. Pat. No. 3,592,194, Issued Jul. 13, 1971; Duncan and Gellert, U.S. Pat. No. 3,489,148, Issued Jan. 13, 1970; Buell, U.S. Pat. No. 3,860,003, Issued Jan. 14, 1975; Weisman and Goldman, U.S. Pat. No. 4,610,678, Issued Sep. 9, 1986; Weisman, Houghton and Gellert; U.S. Pat. No. 4,673,402; Issued Jun. 16, 1987, and Alemany and Berg; U.S. Pat. No. 4,874,735; Issued May 30, 1989, which patents are incorporated herein by reference. A preferred disposable diaper for the purpose of this invention comprises an absorbent core; a topsheet superposed or co-extensive with one face of the core, and a liquid impervious backsheet superposed or co-extensive with the face of the core opposite the face covered by the topsheet. Both the backsheet and the topsheet most preferably have a width greater than that of the core thereby providing side marginal portions of the backsheet and topsheet which extend beyond the core. Frequently the backsheet and the topsheet will be fused together in these side marginal portions. The diaper is preferably constructed in an hourglass or modified hourglass configuration.

The backsheet of the articles herein can be constructed, for example, from a thin, plastic film of polyethylene, polypropylene, or other flexible moisture impeding material which is substantially water impervious. Polyethylene, having an embossed caliper of approximately 1.5 mils, is especially preferred.

The topsheet of the articles herein can be made in part or completely of synthetic fibers or films comprising such materials as polyester, polyolefin, rayon, or the like, or of natural fibers such as cotton. In nonwoven topsheets, the fibers are typically bound together by a thermal binding procedure or by a polymeric binder such as polyacrylate. This sheet is substantially porous and permits a fluid to readily pass therethrough into the underlying absorbent core. The topsheet material will preferably have no affinity for holding aqueous body fluids in the area of contact between the topsheet and the wearer's skin.

Another suitable type of topsheet comprises the topsheets formed from liquid impervious polymeric material such as polyolefins. Such topsheets can have tapered capillaries of certain diameter and taper positioned in the topsheet to permit flow of discharged fluid through the topsheet into the underlying absorbent core of the article.

All of the topsheets used in the articles of the present invention are relatively hydrophobic in comparison with the absorbent core of said articles. Topsheet construction is generally disclosed in Davidson, U.S. Pat. No. 2,905,176, Issued Sep. 22, 1959; Del Guercio, U.S. Pat. No. 3,063,452, Issued Nov. 13, 1962; Holliday, U.S. Pat. No. 3,113,570, Issued Dec. 10, 1963, and Thompson, U.S. Pat. No. 3,929,135; Issued Dec. 30, 1975; which patents are incorporated herein by reference. Preferred topsheets are constructed from polyester, rayon, rayon/polyester blends, polyethylene or polypropylene.

ABSORBENT CORE ELEMENTS

An absorbent core, which itself comprises two or more distinct components, zones or layers, and which is preferably flexible, is positioned between the elongated backing sheet and the topsheet to form the absorbent articles herein. This core essentially comprises both a fluid acquisition/distribution component and a fluid storage/redistribution component. The fluid acquisition/distribution component is positioned within the absorbent article in such a way as to receive or contact aqueous body fluid which has been discharged into the absorbent article by the wearer of the article. The fluid storage/redistribution component in turn is positioned within the article to be in fluid communication with the fluid acquisition/distribution component. In the context of the present invention, it should be noted that the term "fluid" means "liquid."

So long as the acquisition/distribution and storage/redistribution components are in fluid communication with each other, they may be positioned relative to one another in a wide variety of configurations. Most preferred are absorbent cores wherein the acquisition/distribution and storage/redistribution components are in a layered configuration. However other positional relationships between these components are also contemplated. Preferred layer arrangements as well as other alternative absorbent core configurations are described in greater detail hereinafter. The nature of the acquisition/distribution and storage/redistribution components themselves are described in detail as follows:

FLUID ACQUISITION/DISTRIBUTION COMPONENT OF THE ABSORBENT CORE

One essential element of the absorbent core is a fluid acquisition/distribution component which comprises a porous hydrophilic absorbent structure which has certain fluid handling characteristics with respect to discharged aqueous body fluids, e.g., urine, passing onto and into this structure through the article topsheet. This fluid acquisition/distribution component serves to quickly collect and temporarily hold such discharged body fluid. Since such fluid is frequently discharged in gushes, the acquisition/distribution component must be able to quickly acquire and must also preferably transport fluid, e.g., by wicking or other mechanisms, from the point of initial fluid contact to other parts of the acquisition/distribution component for eventual absorption into the adjacent fluid storage/redistribution component.

As indicated, the principal function of the acquisition/distribution component of the absorbent core is to receive fluids passing through the liquid pervious topsheet and to transport such fluids to other areas of the acquisition/distribution component and eventually on to the fluid-holding, foam-based fluid storage/redistribution component of the absorbent core. Accordingly, the fluid acquisition/distribution component should be fashioned from an absorbent material which exhibits an initial Fluid Acquisition Rate of at least about 2 ml of synthetic urine per second. More preferably, the fluid acquisition/distribution component will comprise an absorbent material which exhibits an initial Fluid Acquisition Rate of at least about 6 ml of synthetic urine per second. For purposes of the present invention, the Fluid Acquisition Rate can be determined by a procedure, described more fully hereinafter in the TEST METHODS section, whereby measurements are made of the time taken for aliquots of synthetic urine test liquid deposited onto the surface of an absorbent material to be absorbed into the internal structure of the absorbent material. The "initial" Fluid Acquisition Rate is the time taken for the first aliquot of such test liquid to be absorbed into the absorbent material before such material already contains any of the synthetic urine test liquid.

As noted hereinbefore, material comprising the fluid acquisition/distribution component of the articles herein will preferably also be suitably effective at transporting absorbed liquid from one part or region of the acquisition/distribution component to another. Such liquid transport will frequently arise by virtue of the propensity of the acquisition/distribution component absorbent material to wick liquid through its structure. Accordingly, one measure of the fluid distribution effectiveness of the absorbent material used to form the acquisition/distribution component relates to the ability of such absorbent material to vertically wick synthetic urine.

Vertical wicking effectiveness can be measured and quantified in a number of ways, but one typical indicator of vertical wicking performance is the height to which a vertically positioned test strip of absorbent material will wick synthetic urine from a reservoir within a specified period of time. The fluid acquisition/distribution component of the articles herein will preferably be formed from absorbent material which exhibits a 30-minute Vertical Wicking Height of at least about 2 cm. More preferably, the fluid acquisition/distribution component will comprise absorbent material which has a 30-minute Vertical Wicking Height of at least about 4.5 cm. For purposes of the present invention, Vertical Wicking Height is determined by the procedure described in greater detail in the TEST METHODS section hereinafter.

Any porous hydrophilic absorbent material which will imbibe and transport aqueous body fluids to the extent set forth hereinbefore in terms of Fluid Acquisition Rate and preferably Vertical Wicking Height may be utilized as, or as part of, the fluid acquisition/distribution component of the absorbent articles herein. Frequently such absorbent materials will be foam-based or fiber-based in nature.

One type of absorbent material contemplated for use in or as the fluid acquisition/distribution component in the articles herein comprises hydrophilic, flexible, open-celled polymeric absorbent foam having certain structural characteristics. In particular, absorbent foams useful in or as the fluid acquisition/distribution component are those which have a pore volume of from about 2 to 100 ml/g, a capillary suction specific surface area of from about 0.2 to 1 m$^2$/g; a cell size of from about 10 to 300 microns and a density of from about 0.01 to 0.5 g/cm$^3$, provided values for these parameters are selected so that the absorbent foams exceed the aforementioned Fluid Acquisition Rate minimum. The concepts of foam flexibility, hydrophilicity, pore volume, capillary suction, specific surface area, cell size, and density are described in greater detail hereinafter in connection with the description of foam materials which are to be utilized in or as the fluid storage/redistribution component of the absorbent articles herein.

A more preferred type of absorbent structure for use in or as the fluid acquisition/distribution component comprises non-woven fibrous structures which will provide the fluid handling characteristics hereinbefore set forth. In particular, non-woven structures fashioned from hydrophilic or hydrophilized fibers can be usefully employed as or in the fluid acquisition/distribution component. The most common structures of this type are fibrous webs formed from cellulosic, e.g., wood pulp, fibers. Such webs for example are typically airlaid structures having a dry density of from about 0.04 to 0.3 g/cm$^3$ and a basis weight of from about 0.015 to 0.35 g/cm$^2$. Air laid, non-woven webs of wood pulp fibers of the type are known in the art as "airfelt". One common type of airfelt material fashioned from southern softwood kraft pulp is marketed by The Procter & Gamble Cellulose Company under the name Foley Fluff.

Other types of non-woven structures suitable for use as the fluid acquisition/distribution component include structures such as surfactant-treated bonded carded webs, webs of melt blown synthetic macrofibers or microfibers, pulp coformed webs, staple fiber coformed webs and the like. Structures of this type are described in detail in Latimer et al; European Patent Application No. EP-A-397,110; Published Nov. 14, 1990, incorporated herein by reference.

The most preferred web structures for use as the fluid acquisition/distribution component of the absorbent articles herein are those which are formed from treated cellulose fibers that impart certain web and dry density characteristics to the structures and that are employed in appropriate basis weights. More specifically, the portions or regions of such preferred fiber-based acquisition/distribution component which encounter discharged body fluids will preferably have an average dry density of less than about 0.30 g/cm$^3$, at the point of its use as an absorbent and an average density upon wetting to saturation with synthetic urine (Jayco as described hereinafter), on a dry weight basis, of less than about 0.20 g/cm$^3$, more preferably less than about 0.15 g/cm$^3$. Even more preferably, the average dry density and density upon wetting to saturation will both be between about 0.02 g/cm$^3$ and 0.20 g/cm$^3$, most preferably between about 0.02 g/cm$^3$ and about 0.15 g/cm$^3$. The average dry basis weight of the portion or region of the preferred fiber-based acquisition/distribution components that encounter discharged body fluid will typically range from about 0.001 to about 0.10 g/cm$^2$, more preferably from about 0.01 to about 0.08 g/cm$^2$, most preferably from about 0.015 to about 0.04 g/cm$^2$.

All of the foregoing density and basis weight values are calculated on a dry basis (at equilibrium moisture levels no greater than about 6%). Density and basis weight will generally be substantially uniform throughout the acquisition/distribution component although nonuniform density and/or basis weight, and density and/or basis weight gradients, are also meant to be encompassed herein. Thus, the fluid-absorbing regions of the acquisition/distribution component may contain regions of relatively higher or relatively lower density and basis weight values within the foregoing ranges.

Average density dry and average density upon wetting to saturadrin with synthetic urine values are determined from the basis weight of the dry structure and measurement of the caliper of the dry or wet structure. Both caliper dry and caliper upon wetting to saturation are measured under a confining pressure on the structure of 0.2 psi (1.43 kPa). Average density upon wetting to saturation is calculate from the dry basis weight and caliper of the saturated layer. The caliper of the saturated structure is measured after the structure is saturated (under conditions of no confining pressure) with the synthetic urine test fluid and allowed to equilibrate.

Non-woven fibrous absorbent structures which will provide fluid acquisition/distribution components having the foregoing density and basis weight characteristics are most preferably constructed essentially from hydrophilic chemically stiffened cellulosic fibers. Such cellulosic fibers are typically wood pulp fibers which have been stiffened with an intrafiber chemical stiffening agent and otherwise processed so they are formed into a twisted, curled configuration. Such highly preferred fluid acquisition/distribution component embodiments thus comprise a non-woven fibrous web formed from about 50% to 100% more preferably from about 75% to 100%, by weight of the web of chemically stiffened, twisted, curled cellulosic fibers and from 0% to about 50%, more preferably from 0% to about 25% by weight of a binding agent for such fibers.

For purposes of this invention, the term "chemically stiffened fibers" means any fibers which have been treated by chemical means to increase stiffness of such fibers under both dry and aqueous conditions. Such chemical means include the addition of chemical stiffening agents which, for example, coat and/or impregnate the fibers. Such chemical means also include the stiffening of the fibers by altering the chemical structure of the fibers themselves, e.g., by cross-linking polymer chains within the fibers.

For exemplary purposes, polymeric stiffening agents which can coat or impregnate cellulosic fibers include: cationic modified starch having nitrogen-containing groups (e.g., amino groups) such as those available from National Starch and Chemical Corp., Bridgewater, N.J., USA; latex; wet strength resins such as polyamide-epichlorohydrin resin (e.g., Kymene TM 557H, Hercules, Inc. Wilmington, Del., USA), polyacrylamide resins (described, for example, in Coscia et al; U.S. Pat. No. 3,556,932, Issued Jan. 19, 1971 and also, for example, the commercially available polyacrylamide marketed by American Cyanamid Co., Stanford, Conn., USA, under the tradename Parez TM 631 NC); urea formaldehyde and melamine formaldehyde resins; and polyethylenimine resins. A general dissertation on wet strength resins utilized in the paper art, including those useful herein as fiber stiffening agents, can be found in TAPPI monograph series No. 29. "Wet Strength in Paper and Paperboard", Technical Association of the Pulp and Paper Industry (New York, 1965).

More preferably, the chemically stiffened fibers which can be used in the acquisition/distribution component will be stiffened by means of chemical reaction.

In particular, crosslinking agents can be applied to the fibers which, subsequent to such application, are caused to chemically form intra-fiber crosslink bonds. These crosslink bonds serve to increase stiffness of the fibers.

Fibers stiffened by crosslink bonds in individualized (i.e., fluffed) form are disclosed, for example, in Bernardin, U.S. Pat. No. 3,224,926, Issued Dec. 21, 1965; Chung, U.S. Pat. No. 3,440,135, Issued Apr. 22, 1969; Chatterjee, U.S. Pat. No. 3,932,209, Issued Jan. 13, 1976 and Sangenis et al., U.S. Pat. No. 4,035,147, Issued Jul. 12, 1977. More preferred fibers are disclosed in Dean et al., U.S. Pat. No. 4,822,453, issued Apr. 18, 1989, Dean et al., U.S. Pat. No. 4,888,093, issued Dec. 19, 1989, Moore et al., U.S. Pat. No. 4,898,642, issued Feb. 6, 1990, and Lash et al.; U.S. Pat. No. 4,935,022, Issued Jun. 19, 1990. All of these patents are incorporated herein by reference. In addition to being hydrophilic, these stiffened fibers remain stiff even upon wetting. Thus preferred webs made from these fibers do not collapse, as do webs made from conventional unstiffened fibers when wet. This propensity thus provides the acquisition/distribution layer with the improved ability to acquire and distribute fluids from second and subsequent discharges which are encountered by the acquisition/distribution component.

Suitable fiber-stiffening agents of the cross-linking type comprise monomeric crosslinking agents including, but not limited to, $C_2$–$C_8$ dialdehydes and the $C_2$–$C_8$ monoaldehydes which have an acid functionality. These compounds are capable of reacting with at least two hydroxyl groups in a single cellulose chain or on proximately located cellulose chains in a single fiber. Specific crosslinking agents contemplated for use in preparing the stiffened cellulose fibers include, but are not limited to, glutaraldehyde, glyoxal, formaldehyde, and glyoxylic acid. Other suitable stiffening agents comprise polycarboxylates, such as citric acid. The polycarboxylic stiffening agents and a process for making stiffened fibers using those agents described in U.S. Ser. No. 596,606, filed Oct. 17, 1990 (corresponds to Canadian Patent Specification No. 2028977-5, Available May 8, 1991), incorporated by reference herein.

For the most preferred stiffened cellulosic fibers, chemical processing will involve intrafiber crosslinking with crosslinking agents of the above type while such fibers are in a relatively dehydrated, defibrated (i.e., individualized), twisted, curled condition. The effect of crosslinking under these conditions is to form fibers which are stiffened and which tend to retain their twisted, curled configuration during use in the acquisition/distribution component of the absorbent articles herein.

The extent to which the preferred chemically stiffened fibers are also twisted and curled can be quantified by referencing both a fiber "twist count" and a fiber "curl factor". As used herein, the term "twist count" refers to the number of twist nodes present in a certain length of fiber. Twist count is utilized as a means of measuring the degree to which a fiber is rotated about its longitudinal axis. The term "twist node" refers to a substantially axial rotation of 180° about the longitudinal axis of the fiber, wherein a portion of the fiber (i.e., the "node") appears dark relative to the rest of the fiber when viewed under a microscope with transmitted light. The twist node appears dark at locations wherein the transmitted light passes through an additional fiber wall due to the aforementioned rotation. The distance between nodes corresponds to an axial rotation of 180°.

The number of twist nodes in a certain length of fibers (i.e., the twist count) is directly indicative of the degree of fiber twist, which is a physical parameter of the fiber. The procedures for determining twist nodes and total twist count are described in the hereinbefore referenced U.S. Pat. No. 4,898,642.

The preferred stiffened cellulose fibers will have an average dry fiber twist count of at least about 2.7, preferably at least about 4.5 twist, nodes per millimeter. Furthermore, the average wet fiber twist count of these fibers should preferably be at least about 1.8, preferably at least about 3.0, and should also preferably be at least about 0.5 twist nodes per millimeter less than the average dry fiber twist count. Even more preferably, the average dry fiber twist count should be at least about 5.5 twist nodes per millimeter, and the average wet fiber twist count should be at least about 4.0 twist nodes per millimeter and should also be at least 1.0 twist nodes per millimeter less than its average dry fiber twist count. Most preferably, the average dry fiber twist count should be at least about 6.5 twist nodes per millimeter, and the average wet fiber twist count should be at least about 5.0 twist nodes per millimeter and should also be at least 1.0 twist nodes per millimeter less than the average dry fiber twist count.

In addition to being twisted, the preferred fibers used in the acquisition/distribution component of the absorbent articles herein are also curled. Fiber curl may be described as the fractional shortening of the fiber due to kinks, twists, and/or bends in the fiber. The extent of fiber curling can be quantified by referencing a fiber curl factor. The fiber curl factor, a two dimensional measurement of curl, is determined by viewing the fiber in a two dimensional plane. To determine curl factor, the projected length of the fiber as the longest dimension of a two dimensional rectangle encompassing the fiber, $L_R$, and the actual length of the fiber, $L_A$, are both measured. The fiber curl factor can then be calculated from the following equation:

$$\text{Curl Factor} = (L_A/L_R) - 1.$$

An image analysis method that can be utilized to measure $L_R$ and $L_A$ is described in the hereinbefore referenced U.S. Pat. No. 4,898,642. Preferably the fibers utilized in the acquisition/distribution layer of the absorbent articles herein will have a curl factor of at least about 0.30, and more preferably will have a curl factor of at least about 0.50.

The degree of stiffening, dependent upon the type and amount of stiffening agent (e.g., crosslinking agent) used, the degree of dehydration of the fibers during curing of the crosslinking agent, and the curing time and conditions, affects the ability of the fiber to take up fluid and the tendency of the fiber to swell.

The fiber stiffness can be quantified by referencing the water retention value (WRV) of the stiffened cellulosic fibers used in the acquisition/distribution components of the absorbent articles herein. WRV is a measure of the amount of water retained by a mass of fibers after substantially all of the interfiber water has been removed. Another parameter which can be used to characterize the nature of the stiffened fibers formed by crosslinking fibers in relatively dehydrated form is that of alcohol retention value (ARV). ARV is a measure of the extent to which a fluid, e.g., isopropyl alcohol, which does not induce substantial fiber swelling, is taken up by the stiffened fibers. The ARV of the stiffened fibers is directly related to the extent that the fibers were swollen with the solution of crosslinking agent during the stiffening procedure. Relatively higher ARVs mean that the fibers have been generally swollen to a relatively greater extent during crosslinking. Procedures for determining WRV and ARV are described in the hereinbefore referenced U.S. Pat. No. 4,898,642.

The WRV for the stiffened, twisted, curled fibers which may be used in the preferred acquisition/distribution layers herein will generally range between about 28% and about 50%. In more preferred embodiments, the WRV of the fibers can range from about 30% to 45%. Fibers having a WRV within these ranges are believed to provide an optimal balance of swelling-induced untwisting and fiber stiffness.

The stiffened cellulose fibers preferred for use in the acquisition/distribution component herein are also those which have an ARV (isopropol alcohol) of less than about 30%. The limitation that such fibers have an ARV (isopropol alcohol) of less than about 30% is indicative of the relatively dehydrated, unswollen state of these fibers during the stiffening process. More preferably, the ARV (isopropol alcohol) of the fibers useful in the acquisition/distribution component will be less than about 27%.

The stiffened cellulose fibers herein having the preferred twist count, curl factor, WRV and ARV characteristics hereinbefore set forth, can be prepared by internally crosslinking such fibers in relatively dehydrated form while or after such fibers are being or have been dried and defibrated (i.e., "fluffed") as described in the hereinbefore referenced U.S. Pat. No. 4,898,642. Alternative procedures for preparing hydrophilic, chemically stiffened fibers are those described in the hereinbefore referenced U.S. Pat. Nos. 3,224,926, 3,440,135, 3,932,209, and 4,035,147.

Relative to conventional non-stiffened cellulosic fibers, the crosslinked, twisted, stiffened fibers as hereinbefore described form relatively low tensile strength sheets or webs, particularly in the undried condition. Therefore, in order to facilitate processing and to increase the integrity of the acquisition/distribution component embodiments which are fashioned from stiffened, twisted, curled cellulosic fibers, a binding agent can be integrally incorporated into or onto the acquisition/distribution layer web structure. This can be done by adding the binding agent to the stiffened fibers prior to web formation (wetlaid or airlaid web formations), by applying the binding agent (e.g., chemical additive binding agent) to a wetlaid web after deposition of the web on the forming wire and before drying, by applying binding agent to a dried web (after wet-laying), or by any combination of these binding agent application methods.

Suitable binding agents for addition to or combination with the stiffened cellulosic fibers either by air-laying processes or prior to formation of the wet web from a pulp slurry include, but are not limited to, a variety of cellulosic and synthetic fibrous materials. Such fibrous materials include nonstiffened cellulosic fibers (i.e., conventional cellulosic pulp fibers), highly refined, nonstiffened, cellulosic fibers which are refined to Canadian Standard Freeness (CSF) of less than about 200 CSF, more preferably from about 100 CSF to about 200 CSF and high surface area cellulosic material such as expanded cellulose fibers. Fibrous binding agents of this type are described more fully in U.S. patent application Ser. No. 07/625,776; Filed Dec. 17, 1990 and incorporated herein by reference.

Other types of binding agents which may be utilized in combination with the stiffened cellulosic fibers in the acquisition/distribution component include chemical additive binding agents such as resins, latex materials, starches and modified starches, and thermoplastic binding agents. These types of chemical additive binding agents are also described in greater detail in the aforementioned U.S. Ser. No. 07/625,776. As noted, the binding agent, if present, can comprise up to about 50% by weight of the acquisition/distribution component. More preferably, the binding agent will comprise from about 1% to 25% by weight of the acquisition/distribution component.

The preferred non-woven fibrous acquisition/distribution component structures comprising stiffened, twisted, curled cellulosic fibers, with or without binding agents, can be prepared by either airlaying or wet-laying procedures to form webs of any given desired density and basis weight. Stiffened fiber-containing structures for use in the present invention can be airlaid according to techniques well known to those skilled in the art of airlaying cellulosic fibers. In general, airlaying can be effected by metering an air flow containing the stiffened fibers, in substantially dry condition, onto a wire screen and, optionally, compressing the resulting web to the desired density. Alternately, the fibers can be airlaid to the desired density without compression. The airlaid web will comprise at least about 50% of stiffened cellulosic fibers, as hereinbefore described, and can comprise up to and including 100% of such fibers. The web can optionally contain binding means, also as hereinafter described, or other optional components, such as ingredients modifying fluid handling properties of the webs (e.g., hydrophilic surface active agents), or improving absorbency (e.g., polymeric gelling agents), and the like.

The preferred non-woven fibrous acquisition/distribution component structures comprising stiffened, twisted, curled cellulosic fibers may also be prepared by wetlaying. Techniques for wetlaying cellulosic fibrous material to form sheets such as dry lap and paper are well known in the art. These techniques are generally applicable to the wet-laying of the stiffened fibers to form wetlaid sheets useful in the present invention. Suitable wetlaying techniques include handsheeting, and wetlaying with the utilization of papermaking machines as disclosed, for instance, in Sanford et al.; U.S. Pat. No. 3,301,746; Issued Jan. 31, 1967. Due to the behavior of stiffened fibers, particularly their tendency to flocculate in aqueous slurries, certain processing modifications, hereafter described, are preferably implemented when wetlaying with papermaking machines.

In general, wetlaid webs can be made by depositing an aqueous slurry of fibers on to a foraminous forming wire, dewatering the wetlaid slurry to form a wet web, and drying the wet web. Preferably, the aqueous slurries of fibers for wetlaying will have a fiber consistency of between about 0.05% and about 2.0%, preferably between about 0.05% and about 0.2%, total slurry weight basis. Deposition of the slurry is typically accomplished using an apparatus known in the art as a headbox. The headbox has an opening, known as a slice, for delivering the aqueous slurry of fibers onto the foraminous forming wire. The foraminous forming wire is often referred to in the art as a Fourdrinier wire. The Fourdrinier wire can be of construction and mesh size used for dry lap or other papermaking processing. Preferably, mesh sizes of about 70 to about 100 (Tyler standard screen scale) are used. (All mesh sizes referred to herein shall be based upon the Tyler standard screen scale, unless otherwise specifically indicated.) Conventional designs of headboxes known in the art for drylap and tissue sheet formation may be used. Suitable commercially available headboxes include, for example, fixed roof, twin wire, and drum former headboxes.

Once formed, the wet web is dewatered and dried. Dewatering can be performed with suction boxes or other vacuum devices. Typically, dewatering increases the fiber consistency to between about 8% and about 45%, total wet web weight basis, preferably between about 8% and about 22%. Dewatering to consistencies above about 22% may require wet-pressing and is less preferred. After dewatering, the web can be, but is not necessarily, transferred from the forming wire to a drying fabric which transports the web to drying apparatus. The drying fabric is preferably coarser than the forming wire, for increased drying efficiency. The drying fabric preferably has about 30% to about 50% open area and about 15% to about 25% knuckle area, such as a 31×25 3S (satin weave) fabric that has been sanded to increase the knuckle area to within the preferred range. Wet microcontraction is preferably implemented during transfer from the forming wire to the fabric. Wet microcontraction can be accomplished by running the forming wire at a speed which is from about 5% to about 20% faster than the speed at which the fabric is being run.

Drying can be accomplished with a thermal blow-through dryer or vacuum device such as a suction box, although thermal blow-through drying is preferred. The wetlaid webs are preferably dried to completion (generally to fiber consistency between about 90% and about 95%) by the thermal blow-through dryers. Blow-through drying is believed to efficiently dry webs of the stiffened fibers due to the high void volume of the webs. Steam drum drying apparatus known in the art, such as Yankee drum dryers, can be used but are less preferred. Drum dryers are believed to be less efficient for drying webs of the stiffened fibers and can also compact the webs. The dried webs are preferably not creped.

The web structures containing stiffened, twisted, curled cellulosic fibers, whether airlaid or wetlaid, can be processed into the absorbent cores of the absorbent articles herein in a manner more fully described hereinafter. This procedure will preferably involve associating the non-woven web of stiffened cellulosic fibers as an acquisition/distribution layer overlying a foam-based absorbent structure which forms the fluid storage/redistribution layer component of the absorbent articles herein.

FLUID STORAGE/REDISTRIBUTION COMPONENT OF THE ABSORBENT CORE

In addition to the upper fluid acquisition/distribution component, the absorbent cores of the absorbent articles herein also essentially contain a fluid storage/redistribution component comprising a polymeric absorbent foam material. This fluid storage/redistribution component is maintained in fluid communication with the fluid acquisition/distribution component such that urine or other aqueous body fluids present in the acquisition/distribution component can be absorbed by the polymeric foam material in the fluid storage/redistribution component.

The polymeric foams which are employed in the fluid storage/redistribution component can in general be characterized as the structures which result when a relatively monomer-free gas or relatively monomer-free liquid is dispersed as bubbles in a polymerizable monomer-containing liquid, followed by polymerization of the polymerizable monomers in the monomer-containing liquid which surrounds the bubbles. The resulting polymerized dispersion can be in the form of a porous solidified structure which is an aggregate of cells, the boundaries or walls of which cells comprise solid polymerized material. The cells themselves contain the relatively monomer-free gas or relatively monomer-free liquid which, prior to polymerization, had formed the "bubbles" in the liquid dispersion.

As described more fully hereafter, the preferred polymeric foam materials useful as absorbents in the fluid storage/redistribution component of the absorbent core are those prepared by polymerizing a particular type of water-in-oil emulsion. Such an emulsion is formed from a relatively small amount of a polymerizable monomer-containing oil phase and a relatively larger amount of a relatively monomer-free water phase. The relatively monomer-free, discontinuous "internal" water phase thus forms the dispersed "bubbles" surrounded by the continuous polymerizable monomer-containing oil phase. Subsequent polymerization of the monomers in the continuous oil phase forms the cellular foam structure. The aqueous liquid remaining in the foam structure formed upon polymerization can be removed by pressing and/or drying the foam.

Polymeric foams, including the preferred foams prepared from the water-in-oil emulsions herein, may be relatively closed-celled or relatively open-celled in character, depending upon whether and/or the extent to which, the cell walls or boundaries, i.e., the cell windows, are filled or taken up with polymeric material. The polymeric foam materials useful in the absorbent articles and structures of the present invention are those which are relatively open-celled in that the individual cells of the foam are for the most part not completely isolated from each other by polymeric material of the cell walls. Thus the cells in such substantially open-celled foam structures have intercellular openings or "windows" which are large enough to permit ready fluid transfer from one cell to the other within the foam structure.

In substantially open-celled structures of the type useful herein, the foam will generally have a reticulated character with the individual cells being defined by a plurality of mutually connected, three dimensionally branched webs. The strands of polymeric material which make up the branched webs of the open-cell foam structure can be referred to as "struts." For purposes of the present invention, a foam material is "open-celled" if at least 80% of the cells in the foam structure are in fluid communication with at least one adjacent cell. Alternatively, a foam material can be considered to be substantially open-celled if it has an available pore volume, as described hereinafter, which exceeds the minimum value for this parameter also as set forth hereinafter.

In addition to being open-celled, the polymeric foam absorbents essentially used in the fluid storage/redistribution component of the articles herein are hydrophilic in character. The foams herein must be sufficiently hydrophilic to permit the foam to absorb aqueous body fluids in the amounts hereinafter specified. As discussed hereinafter with respect to preferred foam types and methods of foam preparation, the internal surfaces of the foams herein may be rendered hydrophilic by virtue of the particular monomers selected for use in preparing the polymeric foams, by virtue of residual hydrophilizing agents left in the foam structure after polymerization or by virtue of selected post-polymerization foam treatment procedures which can be used to alter the surface energy of the material which forms the foam structure.

The extent to which polymeric foam structures such as those used in this invention are "hydrophilic" can be quantified by referencing the "adhesion tension" exhibited by such foams in contact with an absorbable test liquid. Adhesion tension is defined by the formula $$AT = \gamma \cos \Theta$$

wherein

AT is adhesion tension in dynes/cm;

$\gamma$ is the surface tension of a test liquid absorbed by the foam material in dynes/cm;

$\Theta$ is the contact angle in degrees between the surface of foam polymer material and the vector which is tangent to the test liquid at the point that the test liquid contacts the foam polymer surface.

For any given hydrophilic foam material, the adhesion tension exhibited by the foam can be determined experimentally using a procedure whereby weight uptake of a test liquid, e.g., synthetic urine, is measured for a foam sample of known dimensions and capillary suction specific surface area. Such a procedure is described in greater detail in the TEST METHODS section hereinafter. The foams which are useful as absorbents in the fluid storage/redistribution component of the present invention are generally those which have been rendered hydrophilic to the extent that they exhibit an adhesion tension of from about 15 to 65 dynes/cm, more preferably from about 20 to 65 dynes/cm, as determined by capillary suction uptake of synthetic urine having a surface tension of 65±5 dynes/cm.

In addition to being "open-celled" and "hydrophilic", the polymeric foam materials useful in the fluid storage/redistribution component of the absorbent articles of the present invention are those which possess performance, e.g., fluid handling, properties which render such foams especially suitable and useful as absorbents for the aqueous body fluids which are introduced into the fluid storage/redistribution component. These fluid handling characteristics are in turn related to and determined by the structural and mechanical characteristics of the absorbent foam materials used herein. Foams having a specific set of structural and mechanical properties can, in fact, be used as absorbents in the fluid storage/redistribution component because they will provide the requisite fluid handling characteristics.

I) Fluid Handling and Absorbency Characteristics

The fluid handling and absorbency characteristics which have been identified as being very relevant to the realization of suitable absorbent foams for the fluid storage/redistribution component are, A) the equilibrium absorbent capacity of the foam, especially under pressure, B) the rate of vertical wicking of fluid through the foam structure, C) the absorbent capacity of the foam at specific reference wicking heights, and D) the ability of the absorbent foam structures to drain (partition) fluid from competing absorbent structures such as the acquisition/distribution component with which the foam will be in fluid communication. Each of these characteristics is described in greater detail as follows:

A) Absorbent Capacity and Absorbent Capacity Under Pressure

Absorbent capacity is the total amount of test fluid (synthetic urine) which a given foam sample will absorb into its cellular structure per unit mass of solid material in the sample. Absorbent capacity under pressure refers to the amount of that fluid held under no confining pressure (free capacity) which the foam will retain within its cellular structure when the foam sample is subjected to compressive force. Such absorbent capacity measurements are for purposes herein calculated at equilibrium, i.e., after the foam sample has been allowed to acquire and/or hold all of the fluid it can over whatever time period is needed to form a completely saturated foam sample with test liquid. The foam materials which are especially useful as absorbents in the fluid storage/redistribution component of the instant absorbent articles such as diapers will exceed a minimum free absorbent capacity and will also exceed a minimum absorbent capacity under pressure.

Using the procedure described in greater detail hereinafter in the TEST METHODS section, free absorbent capacity and absorbent capacity under pressure can both be determined for any given foam sample by a gravimetric analysis technique. In such a technique, a foam sample of specified known size and weight is placed in a dish of test fluid (synthetic urine) and is allowed to absorb the test fluid to equilibrium. After removal of the saturated sample from the fluid, the amount of fluid held per gram of foam, i.e., the measured free capacity, is then calculated. This saturated foam sample is then subjected in step wise fashion to increasing compressive pressure in several increments with the expressed fluid being drained away at each step. The amount of fluid retained in the sample at each pressure loading up to about 1.0 psi (6.9 kPa) is determined gravimetrically.

To be especially useful for absorbing urine in the fluid storage/redistribution component, foam absorbent material should have an equilibrium free capacity of at least about 12, and preferably at least about 20, ml of synthetic urine per gram of dry foam material. Furthermore the capacity of such foam materials under a confining pressure of about 0.74 psi (5.1 kPa) maintained for 15 minutes at 37° C. should be at least about 5%, more preferably at least about 20%, of the equilibrium free capacity of such foams.

B) Vertical Wicking Performance

Yet another fluid handling attribute of the absorbent foams useful in the fluid storage/redistribution component relates to their ability to relatively quickly move or transport acceptable amounts of body fluids through their foam structures. Vertical wicking, i.e., fluid wicking in a direction opposite from gravitational force, is one measure of the especially desirable performance attribute of fluid transport for the storage/redistribution component absorbent foam materials herein. This is because such materials will frequently be utilized in fluid storage/redistribution components in a manner that absorbed fluid must be moved, i.e., "redistributed," within the foam from a relatively lower position to a relatively higher position within the storage/redistribution component of the absorbent core. Vertical wicking is believed to contribute to this fluid redistribution propensity of the foams which are useful herein.

Vertical wicking performance is related to the magnitude of the capillary suction driving force which moves liquid through the foam and holds it in the foam structure. Foam characterizing parameters which relate to vertical wicking propensity thus provide an indication as to how well preferred foams herein will perform as storage/redistribution component absorbents in absorbent articles. For the storage/redistribution component foam absorbents of the present invention, fluid wicking propensity can be quantified by referencing both a vertical wicking rate test and a vertical wicking absorbent capacity test.

1) Vertical Wicking Rate

The vertical wicking rate test measures the time taken for a colored test liquid (e.g., synthetic urine) from a reservoir to wick a vertical distance of 5 cm through a test strip of foam of specified size when the test is performed at 37° C. Such a vertical wicking rate test is described in greater detail in the TEST METHODS section hereinafter. To be especially useful for absorbing urine in the storage/redistribution component, the storage/redistribution component foam absorbents will preferably have a 5 cm vertical wicking rate of no more than about 30 minutes when wicking synthetic urine (65±5 dynes/cm). More preferably, the preferred foam absorbents of the present invention will have a 5 cm vertical wicking rate of no more than about 5 minutes when wicking synthetic urine.

2) Vertical Wicking Absorbent Capacity

The vertical wicking absorbent capacity test is carried out in conjunction with the vertical wicking rate test. Vertical wicking absorbent capacity measures the amount of test fluid per gram of absorbent foam that is wicked to each one inch (2.54 cm) vertical section of the same standard size foam sample used in the vertical wicking rate test. Such a determination is generally made after the sample has been allowed to vertically wick test fluid to equilibrium (e.g., after about 18 hours). Like the vertical wicking rate test, the vertical wicking absorbent capacity test is described in greater detail hereinafter in the TEST METHODS section.

To be especially useful for absorbing urine in the storage/redistribution component, the preferred storage/redistribution component foam absorbents of the present invention will generally have a vertical wicking absorbent capacity such that, at 11.4 cm (4.5 inches) of vertical wicking height, the foam test strip has an absorbent capacity of at least about 10 ml of synthetic urine (65±5 dynes/cm) per gram of absorbent foam. More preferably, the preferred storage/redistribution component foam absorbents herein will have a vertical wicking absorbent capacity at 11.4 cm (4.5 inches) of from about 20 to 45 ml of synthetic urine per gram of foam.

C) Partitioning

It is, of course, desirable for the storage/redistribution component foams of this invention to have a propensity for pulling body fluids into the foam structure from other absorbent article components such as the fluid acquisition/distribution component which also are absorbing such fluids. Such a propensity to drain fluid from other absorbent article components is known in the art as "partitioning." The concept of partitioning and certain procedures for determining partitioning performance are described, for example, in Weisman/Goldman; U.S. Pat. No. 4,610,678; Issued Sep. 9, 1986. When tested for partitioning performance using procedures similar to those disclosed in U.S. Pat. No. 4,610,678, the absorbent foam structures of the fluid storage/redistribution component should exhibit especially desirable fluid partitioning characteristics relative to the absorbent materials used in the fluid acquisition/distribution component of the articles herein.

II) Structural Features of Preferred Storage/Redistribution Component Foams

Specific somewhat interrelated and interdependent structural properties of foam absorbents have been identified as being highly desirable in foams which are especially suitable for absorbing aqueous body fluids in the storage/redistribution component of the absorbent articles herein. It should be understood that the foam materials of the storage/redistribution component may have structural properties which are different from those specified hereinafter at some point prior to contact between the foam and the aqueous body fluid to be absorbed in the storage/redistribution component. For example, during their manufacture, shipping, storage, etc., the foams herein may have pore volume, specific surface area, density and/or cell size values outside of the ranges set forth hereinafter for these parameters. However, such foam absorbent structures are nevertheless still within the scope of this invention if they later undergo physical or rheological changes so that they then have the values specified hereinafter for these structural properties at least at some point during the period of subsequent contact between the foam and the aqueous body fluid it encounters in the storage/redistribution component. The several structural properties of the foam absorbents preferred for use in the storage/redistribution component of the articles herein can be summarized as follows:

A) Pore Volume

Pore volume is a measure of the volume of the openings or cells in a porous foam structure per unit mass of solid material (polymer structure plus any residual solids) which forms the foam structure. Pore volume can be important in influencing a number of performance and mechanical features of the absorbent foams herein. Such performance and mechanical features include absorbent capacity of the foams for aqueous body fluids, the extent and rate of fluid distribution within the structure by wicking of absorbed aqueous fluids from one part of the absorbent foam to another, foam flexibility and foam compression deflection characteristics.

Pore volume may be determined by any suitable experimental method which will give an accurate indication of the actual pore volume of the structure. Such experimental methods will generally involve the measurement of the volume and/or mass of a test liquid which can be introduced into the foam structure and which therefore is representative of the volume occupied by the open cells of the foam. For this reason the pore volume parameter of the foams useful in the fluid storage/redistribution component herein may also be referred to as "available pore volume."

One conventional way for determining available pore volume experimentally involves the introduction of a low surface tension liquid such as isopropanol into the foam structure from outside the foam structure. A procedure for determining available pore volume using isopropanol is set forth hereinafter in the TEST METHODS section. It should be understood, however, that alternative test liquids and procedures may also be used to determine available pore volume.

The pore volume of the absorbent foams useful in the fluid storage/redistribution component can be influenced and controlled by adjusting a number of foam composition and processing features. For example, with the preferred HIPE emulsion-based foams herein, these pore volume influencing features can include the water-to-oil ratio of the HIPE emulsion, type and amount of water phase electrolyte used, type and amount of oil phase emulsifier used, post-polymerization foam compression steps to effect washing and/or densification of the foam and degree of recovery of the polymerized foam structure after such compression steps.

The foam materials used in the fluid storage/redistribution component of the articles herein will generally have a pore volume of from about 12 to 100 ml/g; more preferably from about 20 to 70 ml/g and most preferably from about 25 to 50 ml/g. Such ranges for pore volume are intended to be an "inclusive" definition of theoretical pore volume for the foams encompassed by this invention. Thus if any experimental method which can reasonably be expected to give measurements approximating theoretical pore volume provides values within the foregoing ranges, then the foam materials tested by any such method are within the scope of this invention.

B) Capillary Suction Specific Surface Area

Another structural feature of the preferred foam materials suitable for use in the fluid storage/redistribution component is a certain capillary suction specific surface area. Capillary suction specific surface area is, in general, a measure of the test-liquid-accessible surface area of the polymeric network forming a particular foam per unit mass of the bulk foam material (polymer structural material plus solid residual material). Capillary suction specific surface area is determined both by the dimensions (i.e., diameter) of the cellular units in the foam and by the size (length, width and thickness) of the struts which form such cellular units. Capillary suction specific surface area is thus a way of quantifying the total amount of solid surface provided by the foam network to the extent that such a surface participates in absorbency.

The capillary suction specific surface area of an open-celled foam structure such as the absorbent foams of the storage/redistribution component is the feature of the foam that influences the capillarity (or capillary suction) exhibited by the foam. It has been found that foam capillarity must be controlled and selected so that the storage layer foam materials herein have sufficient capillarity to provide acceptable fluid retention while still allowing some transport, e.g., by wicking, of the fluid to occur within the foam structure of the fluid storage/redistribution component. Adjustment of capillary suction specific surface area, as well as control of the hydrophilicity of the foam polymer surfaces, is thus the means for providing the requisite degree of capillarity for the storage/redistribution component absorbent foams of this invention. Foams of relatively high capillary suction specific surface area provide the very desirable combination of high capacity (and low density) and high capillarity. High specific surface area is a consequence of the fineness of the struts making up the foam structure.

The capillary suction specific surface area of the storage/redistribution component foams is influenced and controlled by adjusting many of the same composition and processing parameters which affect the foam pore volume. For HIPE emulsion-based foams, these composition parameters include the water-to-oil ratio of the HIPE emulsion, and the type and amounts of monomers, emulsifiers, and electrolytes utilized in the HIPE emulsion. Process parameters affecting capillary suction specific surface area include mixing energy and temperature.

As noted, for purposes of this invention, the specific surface area of any given foam material being contemplated for use as or in the fluid storage/redistribution component of the absorbent articles herein can and will usually be determined by a procedure which involves the principle of capillary suction. In such a procedure, capillary suction specific surface area is determined by measuring the amount of capillary uptake of a low surface tension liquid (e.g., ethanol) which occurs within a foam sample of a known mass and dimensions. A detailed description of such a procedure for determining foam specific surface area via the capillary suction method is set forth in the TEST METHODS section hereinafter. Any reasonable alternative method for determining capillary suction specific surface area may also be utilized.

The open-celled, porous absorbent foams which are useful in the fluid storage/redistribution component are generally those which are prepared to have certain capillary suction specific surface area characteristics. In particular, the storage/redistribution component foams herein should have a capillary suction specific surface area ranging from about 0.5 to 5.0 $m^2/g$, more preferably from about 0.75 to 4.5 $m^2/g$, most preferably from about 1.0 to 4.0 $m^2/g$. It has been discovered that hydrophilic foams having such capillary suction specific surface area values will generally possess an especially desirable balance of absorbent capacity, fluid-retaining and fluid-wicking or distribution characteristics for aqueous body liquids such as urine so as to render such foams particularly useful in the fluid storage/redistribution component.

C) Supplemental or Alternative Structural Features

Two additional structural features of the storage/redistribution component absorbent foams herein which are interrelated with pore volume and capillary suction specific surface area and which can be used as supplemental or alternative ways of characterizing the preferred storage/redistribution component foams of this invention are foam density and the average size or diameter of the cells making up the foam. Each of these two supplemental/alternative structural features is described as follows:

1) Foam Density

Density of the storage/redistribution component foam materials herein, like pore volume and capillary suction specific surface area, can influence a number of performance and mechanical characteristics of these foams. These include absorbent capacity for aqueous body fluids, extent and rate of fluid distribution within the foam and foam flexibility and compression deflection characteristics. Importantly also, the density of the storage/redistribution component foam absorbent materials herein can determine the cost effectiveness of the absorbent articles herein.

Foam density in grams of foam material per cubic centimeter of foam volume in air is specified herein on a dry basis. Thus the amount of absorbed aqueous liquid, e.g., that residual liquid which may be left in the foam, for example, after HIPE emulsion polymerization, washing and/or hydrophilization, is disregarded in calculating and expressing foam density. Foam density as specified herein does include, however, residual solid material such as electrolyte, emulsifiers, hydrophilizing agents, etc., in the polymerized foam. Such residual material may, in fact, contribute significant mass to the foam material.

Any suitable gravimetric procedure which will provide a determination of mass of solid foam material per unit volume of foam structure can be used to measure foam density. For example, an ASTM gravimetric procedure described more fully in the TEST METHODS section hereinafter is one method which may be employed for density determination. For those situations where the foam sample preparation procedures (drying, aging, preflexing, etc.,) might inadvertently alter the density measurements obtained, then alternate density determination tests may also be utilized. Such alternative methods, for example, might include gravimetric density measurements using a test liquid absorbed within the foam material. This type of density determination method can be useful for characterizing very low density foams such as the foams herein wherein the dry density approximates the inverse of the pore volume of the foam. [See Chatterjee, "Absorbency," *Textile Science and Technology*, Vol. 7, 1985, p. 41.] As with pore volume and capillary suction specific surface area, the ranges for foam density set forth hereinafter are intended to be inclusive, i.e., they are intended to encompass density values that may be determined by any reasonable experimental test method.

The storage/redistribution component foam absorbents of the present invention will preferably have dry basis density values which range from about 0.01 to 0.08 g/cm$^3$, more preferably from about 0.014 to about 0.05 g/cm$^3$, and most preferably from about 0.02 to 0.04 g/cm$^3$, at the time such foam absorbents encounter aqueous fluids to be absorbed. Density of the storage/redistribution component foam materials can be adjusted to within the foregoing ranges by controlling many of the same foam composition and processing parameters set forth hereinbefore for pore volume adjustment. Density of the storage/redistribution component absorbent foam structures herein need not be uniform throughout the structure. Some portions or zones of the foam structure may have relatively higher or lower densities than other portions or zones thereof.

2) Cell Size

Another alternative or supplemental structural feature of the storage/redistribution component absorbent foams herein, which is not an essentially established parameter but which may be useful in defining preferred storage/redistribution component foam materials of this invention, is cell size. Foam cells, and especially cells which are formed by polymerizing a monomer-containing oil phase that surrounds relatively monomer-free water-phase bubbles, will frequently be substantially spherical in shape. The size or "diameter" of such substantially spherical cells is thus yet another commonly utilized parameter for characterizing foams in general as well as for characterizing certain preferred absorbent foams of the type utilized in the present invention. Since cells in a given sample of polymeric foam will not necessarily be of approximately the same size, an average cell size, i.e., average cell diameter, will often be specified.

As with foam density, capillary suction specific surface area and pore volume, cell size is a foam parameter which can also impact on a number of important mechanical and performance features of the storage/redistribution component absorbent foam material of this invention. Since cell size is a factor, along with capillary suction specific surface area, pore volume and foam hydrophilicity, that determines the capillarity of the foam, cell size is a foam structure parameter that can directly affect both the absorbent capacity and the internal fluid transport properties of the storage/redistribution component foam absorbents herein. Cell size can also affect mechanical properties of the storage/redistribution component foams herein including such features as flexibility and resistance to and recovery from compression deflection.

A number of techniques are available for determining average cell size in foams. These techniques include mercury porosimetry methods which are well known in the art. The most useful technique, however, for determining cell size in foams involves simple photographic measurement of a foam sample. Figure of the drawings, for example, is a photomicrograph of a fracture surface of a typical HIPE foam absorbent structure useful in the present invention. Superimposed on the photomicrograph is a scale representing a dimension of 10 microns. Such a scale can be used to determine average cell size via an image analysis procedure. Image analysis of photomicrographs of foam samples is, in fact, a commonly employed analytical tool which can be used to determine average cell size of the storage/redistribution component foam structures herein. Such a technique is described in greater detail in Edwards et al; U.S. Pat. No. 4,788,225; Issued Nov. 29, 1988. This patent is incorporated herein by reference.

As determined by direct photographic measurement, the foams useful as absorbents for aqueous body fluids in the fluid storage/redistribution component in accordance with the present invention will preferably have an average cell size ranging from about 5 to 100 microns. More preferably, cell size will range from about 10 to 90 microns. Most preferably, cell size will be between about 15 and 80 microns.

Size or diameter of the cells in the storage/redistribution component foam absorbents herein can be influenced and controlled by variation of the same type of foam composition and processing features that influence capillary suction specific surface area and available pore volume. For the preferred HIPE-based foams, these include primarily those factors which determine the size of the water-phase "bubbles" in the HIPE emulsion precursor of the polymeric foam structures herein. Thus, cell size can be varied by adjusting water-to-oil ratio of the HIPE emulsion, and the type and amount emulsifier used to form the HIPE emulsion. Cell size may also be altered by simply compressing the solid foam structures after they have been prepared.

As indicated hereinbefore, the dimensions of cells in the storage/redistribution component absorbent foams of this invention will generally not be uniform so an average cell size for any given foam sample or zone in a foam sample can and should be calculated. It is, of course, possible to utilize absorbent foams in the fluid storage/redistribution component which have discrete, identifiable zones of relatively larger or relatively smaller average cell size.

III) Mechanical Features

Absorbent foams having suitable polymeric composition and the structural features hereinbefore described will, in general, possess mechanical properties, e.g., resistance to compression deflection, flexibility, recovery from compression deflection, integrity, softness, etc., which render such foams suitable for use in the fluid storage/redistribution component of absorbent articles such as disposable diapers. Within the aforementioned structural limitations, however, it is possible to select certain combinations of parameters and/or certain foam preparation techniques and conditions which provide storage/redistribution component foam absorbents that exhibit especially desirable mechanical properties. The specific, somewhat interrelated mechanical properties which have been identified as contributing to the realization of absorbent foams especially suitable for use in absorbent articles for incontinence management can be summarized as follows:

A) Resistance to Compression Deflection

The most important mechanical feature of the polymeric foams used in or as the fluid storage/redistribution component is the strength of the foam absorbent as determined by its resistance to compression deflection. The resistance to compression deflection exhibited by the storage/redistribution component foam absorbents herein is a function of the polymer elastic modulus and the dimensions of the "struts" which form the foam network. The elastic modulus of the struts is, in turn, determined by a) the polymeric composition of the struts and b) the extent to which the struts may be plasticized by residual material, e.g., emulsifiers, synthesis water phase or subsequently added hydrophilizing agents, left in the foam structure after processing.

To be useful as absorbent structures in absorbent articles such as diapers, the storage/redistribution component absorbent foam materials must be suitably resistant to deformation or compression by forces encountered when such absorbent materials are engaged in the absorption and retention of fluids. Foams which do not possess sufficient foam strength in terms of resistance to compression deflection may be able to acquire and store acceptable amounts of body fluid in the storage/redistribution component under no-load conditions but will too easily give up such fluid under the compressive stress caused by the motion and activity of the wearer of the absorbent articles which contain the foam in the storage/redistribution component.

The resistance to compression deflection exhibited by the foam absorbents used in the fluid storage/redistribution component of the present invention can be quantified by determining the amount of strain produced in a sample of saturated foam material held under a certain confining pressure for a specified period of time. For purposes of the present invention such measurements can be made on a foam sample of standard size (cylinders which are 0.8 cm thick and have a cross-sectional circular area of 6.5 cm$^2$). Such samples are saturated with synthetic urine having a surface tension of 65±5 dynes/cm and are thereafter subjected to a confining pressure of 5.1 kPa for a period of 15 minutes at a temperature of 37° C. The amount of strain produced in such testing is reported as a percentage of the original sample thickness that the compressed thickness of the sample represents. The method for carrying out this particular type of test for quantifying resistance to compression deflection is set forth hereinafter in greater detail in the TEST METHODS section.

The storage/redistribution component absorbent foams useful herein are those which exhibit a resistance to compression deflection such that a confining pressure of 5.1 kPa produces a strain of from about 5% to 95% compression of the foam structure when it has been saturated to its free absorbent capacity with synthetic urine having a surface tension of 65±5 dynes/cm. Preferably the strain produced under such conditions will range from about 5% to 75%, most preferably from about 5% to 50%. For the preferred HIPE storage/redistribution component foams of this invention, resistance to compression deflection can be adjusted to strain values within the foregoing ranges by appropriate selection of monomer, comonomer and cross-linker types and concentrations in combination with selection of appropriate emulsion formation and emulsion polymerization conditions and techniques. Thus, such preferred foams can be formed from materials with elastic modulii large enough to provide adequate resistance to compression deflection even though such foams are low density and have very fine struts to provide high specific surface area.

B) Flexibility

The storage/redistribution component absorbent foams of the present invention must be sufficiently flexible so that they can be utilized in absorbent products that will conform to the body shape of the wearer. Characterization of the storage/redistribution component absorbent foams herein as flexible, therefore, means that these foams can be deformed or bent to the extent necessary for use in such absorbent articles without significant damage to their structural integrity or significant loss of their absorbent properties.

Preferred storage/redistribution component absorbent foams must also be sufficiently flexible to withstand compressive or deforming forces which are encountered during preparation, processing, packaging, shipping and storing of absorbent articles containing such foam materials. Disposable diapers, for example, are generally packaged and marketed in a folded condition wherein the diaper core is folded in both the longitudinal and transverse directions. Disposable diapers are also generally marketed in the form of stacks of folded diapers, which stacks are contained and compressed by their surrounding packaging. Accordingly, the compressive and deforming forces to which the storage/redistribution component foam absorbents herein may be subjected during processing and marketing may be even greater than those which are applied to the foam materials in use.

Given the nature of treatment which the storage/redistribution component absorbent foams herein must withstand, preferred storage/redistribution component absorbent foam materials of this invention will possess flexibility characteristics which can be quantified by referencing their ability to withstand bending without undergoing significant damage to their structural integrity. Described in the TEST METHODS section hereinafter is a procedure for determining the flexibility of the storage/redistribution component absorbent foams herein by determining whether and how many times a foam sample of a given specified size can be bent around a cylindrical mandrel at a specified rate without breaking. The preferred storage/redistribution component foams of this invention are those which are flexible enough so that, at their point of use as an absorbent for body fluids, the saturated foam material at 37° C. can be subjected to this bending test without breaking (i.e., exhibit a bending value of at least one cycle). More preferably, preferred foams can be bent at least 2 times, even more preferably at least 5 times without breaking when subjected to such a test procedure.

C) Preferred or Supplemental Mechanical Properties

In addition to their resistance to compression deflection and flexibility characteristics, the preferred foam absorbents used in the fluid storage/redistribution component will also possess several additional types of mechanical attributes. These preferred mechanical attributes include desirable recovery from compression deflection (i.e., resilience), foam integrity, and softness to the touch. Each of these preferred mechanical properties is described in greater detail as follows:

1) Recovery From Compression Deflection

Recovery from compression deflection relates to the tendency or propensity of a piece of foam material to return to its original dimensions after being deformed or compressed under forces encountered in manufacture, storage or use. For purposes of the present invention, recovery from compression deflection of the preferred storage/redistribution component foam absorbents herein should be determined on foams which are at their appropriate point-of-use density, and frequently under such conditions, the foam will contain absorbed body fluid. Accordingly, recovery from compression deflection may be measured on foams which are either dry or saturated with synthetic urine.

A suitable procedure for determining recovery from compression deflection is set forth in the TEST METHODS section hereinafter. Such a procedure in general involves compression and release of a standard size foam sample which is either dry or has been saturated to its free absorbent capacity with synthetic urine. Samples are maintained under 50% compression for a set period of time and then are released from compression. The extent to which the sample recovers its thickness in the one-minute period after the release of compressive force is taken as a measure of the recovery from compression deflection (resilience) propensity of the sample.

Preferred absorbent foams useful in the fluid storage/redistribution component will generally exhibit a recovery of at least 85% of original caliper when dry and/or at least 75% of original caliper when wet after one minute. More preferably, such preferred storage/redistribution component foam materials will have a recovery form compression deflection of at least 90% dry and/or 80% wet.

2) Foam Integrity and Softness

While not absolutely essential for the realization of operable or useful absorbent structures, the storage/redistribution component foam absorbents of this invention will preferably possess the additional mechanical attributes of structural integrity in use and softness (lack of irritation) to the touch. For example, storage/redistribution component foam materials that will be employed in such absorbent articles as infant diapers will frequently be subjected to both dynamic and static forces which arise when the wearer walks, runs, crawls or jumps. Such forces may not only tend to compress the storage/redistribution component foam absorbents and expel fluid therefrom, but such forces may also tend to rip or tear or otherwise fragment the foam structure. Obviously, it would be advantageous for foam structures which are to be used in this manner to have sufficient structural integrity to minimize the incidence of foam tearing or fragmenting in use.

The storage/redistribution component foam elements of this invention may also be used in absorbent articles in configurations wherein even the storage/redistribution component foam material surface may come into close proximity to the wearer's skin. Accordingly, it would be very desirable for the surface of the storage/redistribution component foam absorbents herein to be acceptably soft and non-irritating to the touch.

IV) Preferred HIPE Absorbent Foams For Storage/Redistribution Component Use

As noted hereinbefore, especially preferred storage/redistribution component absorbent foam materials which can be prepared to have the requisite fluid handling characteristics and the preferred structural/mechanical properties as hereinbefore described are the products which result from polymerization of certain water-in-oil emulsions having therein a relatively high ratio of water phase to oil phase. Emulsions of this type which have these relatively high water to oil phase ratios are known in the art as high internal phase emulsions ("HIPEs" or "HIPE" emulsions). The preferred storage/redistribution component polymeric foam materials which result from the polymerization of such emulsions are referred to herein as "HIPE foams."

The relative amounts of the water and oil phases used to form the polymeric foam precursor HIPE emulsions are, among many other parameters, important in determining the structural, mechanical and performance properties of the resulting preferred polymeric foams for the storage/redistribution component. In particular, the ratio of water to oil in the foam-forming emulsion can influence foam density, cell size, specific surface area of the foam and dimensions of the struts which form the foam. The emulsions used to prepare the preferred polymeric HIPE foam materials for the fluid storage/redistribution component will generally have water-to-oil phase ratios ranging from about 12:1 to 100:1; more preferably from about 20:1 to 70:1; most preferably from about 25:1 to 50:1.

The continuous oil phase of the emulsions used to prepare the preferred HIPE storage/redistribution component foams herein comprises the monomers that are to be polymerized to form the solid foam structure. Such monomers include a principal monomer component, a comonomer component and a cross-linking agent component. Selection of particular types and amounts of monofunctional principal monomer(s) and comonomer(s) and polyfunctional cross-linking agent(s) can be important to the realization of absorbent HIPE foam materials having the desired combination of structure, mechanical, and fluid handling properties which render such materials suitable for use in the fluid storage/redistribution component.

The principal monofunctional monomer component utilized in the oil phase of the preferred foam-precursor HIPE emulsions comprises one or more monomers that tend to impart glass-like properties to the eventually resulting foam structure. Such monomers are hereinafter referred to as "glassy" monomer,, and are, for purposes of this invention, defined as monomeric materials which would produce high molecular weight (greater than 6000) homopolymers having a glass transition temperature, $T_g$, above about 40° C. The preferred monofunctional glassy monomer type is a styrene-based monomer with styrene itself being the most preferred monomer of this kind. Substituted, e.g., monosubstituted, styrene such as p-methylstyrene may also be employed. The monofunctional glassy monomer component will normally comprise from about 3% to 41%, more preferably from about 7% to 40% by weight of the oil phase used to form the HIPE emulsion to be polymerized.

The monofunctional comonomer component, which will also be present in the oil phase of the HIPE emulsion along with the glassy principal monomer material, comprises one or more comonomers which tend to impart rubber-like properties to the eventually resulting foam structure. Such comonomers are hereinafter referred to as "rubbery" comonomers and are, for purposes of this invention, defined as monomeric materials which would produce high molecular weight (greater than 10,000) homopolymers having a glass transition temperature, $T_g$, of about 40° C. or lower. Monofunctional rubbery comonomers of this type include, for example, alkyl-acrylates, alkylmethacrylates, allylacrylate, butadiene, substituted butadienes, vinylidine halides and combinations of such comonomers and comonomer types. Preferred rubbery comonomers include butylacrylate, 2-ethylhexylacrylate, butadiene, isoprene and combinations of these comonomers. Of all of these species, butylacrylate and 2-ethylhexylacrylate are the most preferred. The monofunctional rubbery comonomer component will generally comprise from about 27% to 73%, more preferably from about 27% to 66%, by weight of the oil phase.

In the HIPE emulsions used to form the preferred storage/redistribution component absorbent foams herein, both the monofunctional glassy principal monomer(s) and the monofunctional rubbery comonomer(s) must be present in the oil phase within the hereinbefore recited concentration ranges. In addition, the molar ratio of monofunctional glassy monomer component to the monofunctional rubbery component will generally range from about 1:25 to 1.5:1, more preferably from about 1:9 to 1.5:1.

Since the polymer chains formed from the glassy monomer(s) and the rubbery comonomer(s) are to be cross-linked, the oil phase of the emulsions used to form the preferred HIPE storage/redistribution component foams herein must also contain a polyfunctional cross-linking agent. As with the monofunctional monomers and comonomers, selection of a particular type and amount of cross-linking agent is very important to the eventual realization of preferred polymeric foams having the desired combination of structural, mechanical, and fluid-absorbing properties.

Depending upon the type and amounts of monofunctional monomers and comonomers utilized, and depending further upon the desired characteristics of the eventually realized preferred polymeric storage/redistribution component foams, the polyfunctional crosslinking agent component for use in the preferred HIPE emulsion foam precursor can be selected from a wide variety of polyfunctional, preferably difunctional, monomers. Thus, the cross-linking agent may be a divinyl aromatic material such as divinylbenzene, divinyltoluene or diallylphthalate. Alternatively, divinyl aliphatic cross-linkers such as any of the diacrylic acid esters of polyols can be utilized. The cross-linking agent found to be suitable for preparing the most acceptable foam from the preferred HIPE emulsions herein is divinylbenzene.

The cross-linking agent of whatever type will generally be employed in the oil phase of the preferred foam-forming emulsions herein in an amount of from about 8% to 40%, more preferably from about 10% to 25%, by weight. Amounts of cross-linking agent(s) within such ranges will generally provide a cross-linker molar concentration of from about 5 mole percent to about 60 mole percent, based on total monomers present in the oil phase.

The major portion of the oil phase of the preferred HIPE emulsions herein will comprise the aforementioned monomers, comonomers and cross-linking agents which eventually form the preferred polymeric storage/redistribution component foam absorbents. It is therefore essential that these monomers, comonomers and cross-linking agents be substantially water-insoluble so that they are primarily soluble in the oil phase and not the water phase. Use of such substantially water-insoluble monomer materials ensures that preferred HIPE emulsions of appropriate characteristics and stability will be realized.

It is, of course, preferred that the monomers, comonomers and cross-linking agents used to form the preferred polymeric foam materials for the storage/redistribution component herein be of the type such that the eventually formed foam polymer is suitably non-toxic and appropriately chemically stable. Thus, such monomers, comonomers and cross-linking agents should preferably have little or no toxicity in the very low residual concentrations wherein they may be encountered during post-polymerization foam processing and/or use.

Another essential component of the oil phase of the HIPE emulsions used to form the preferred polymeric storage/redistribution component foams of the present invention comprises an emulsifier which permits formation of stable HIPE emulsions. Such emulsifiers are those which are soluble in the oil phase used to form the emulsion. Emulsifiers utilized may be nonionic, cationic, anionic or amphoteric provided the emulsifier or combination of emulsifiers will form a stable emulsion. Preferred types of emulsifiers which can be used to provide an emulsifier component having suitable characteristics include the sorbitan fatty acid esters, polyglycerol fatty acid esters, polyoxyethylene (POE) fatty acids and esters. Especially preferred are the sorbitan fatty acid esters such as sorbitan monolaurate (SPAN ® 20), sorbitan monooleate (SPAN ® 80) and combinations of sorbitan monooleate (SPAN ® 80) and sorbitan trioleate (SPAN ® 85). One such particularly preferred emulsifier combination comprises the combination of sorbitan monooleate and sorbitan trioleate in a weight ratio greater than or equal to about 3.1, more preferably about 4:1. Other operable emulsifiers include TRIODAN ® 20 which is a commercially available polyglycerol ester marketed by Grindsted and EMSORB 2502 which is a sorbitan sesquioleate marketed by Henkel.

The emulsifier component will generally comprise from about 2% to 33% by weight of the oil phase used to form the HIPE emulsions which in turn are used to prepare the preferred polymeric storage/redistribution component foams herein. More preferably, the emulsifier component will comprise from about 4% to 25% by weight of the oil phase.

In addition to the monomeric and emulsifier components hereinbefore described, the oil phase used to form polymerizable HIPE emulsions herein may also contain additional optional components. One such optional oil phase component may be an oil soluble polymerization initiator of the general type hereinafter described. Another possible optional component of the oil phase may be a substantially water insoluble solvent for the oil phase monomer and emulsifier components. A solvent of this type must, of course, not be capable of dissolving the eventually polymerized monomers. Use of such a solvent is not preferred, but if such a solvent is employed, it will generally comprise no more than about 10% by weight of the oil phase.

As indicated, the HIPE oil phase as hereinbefore described is the continuous phase in the emulsions to be polymerized to realize the preferred storage/redistribution component foams of the present invention. The discontinuous internal phase of the polymerizable HIPE emulsions is the water phase which will generally be an aqueous solution containing one or more dissolved components. One essential dissolved component of the water phase is a water-soluble electrolyte. The dissolved electrolyte in the water phase of the HIPE emulsion serves to minimize the tendency of monomers and crosslinkers which are primarily oil soluble to also dissolve in the water phase. This, in turn, can minimize the extent to which, during polymerization of the emulsion, polymeric material fills the cell windows at the oil/water interfaces formed by the water phase bubbles. Thus the presence of electrolyte and the resulting ionic strength of the water phase can determine whether and to what degree the resulting preferred polymeric storage/redistribution component foams may be open-celled.

Any electrolyte which provides ionic species to impart ionic strength to the water phase may be used. Preferred electrolytes are mono-, di-, or tri-valent inorganics salts such as the water-soluble halides, e.g., chlorides, nitrates and sulfates of alkali metals and alkaline earth metals. Examples include sodium chloride, calcium chloride, sodium sulfate and magnesium sulfate. Calcium chloride is the most preferred for use in these preferred embodiments of the present invention.

Generally electrolyte will be utilized in the water phase of the HIPE emulsions which are precursors to the preferred polymeric storage/redistribution component foams herein in a concentration which ranges from about 0.2% to about 40% by weight of the water phase. More preferably, the electrolyte will comprise from about 0.5% to 20% by weight of the water phase.

The HIPE emulsions used to prepare the preferred polymeric storage/redistribution component foams herein will also typically contain a polymerization initiator. Such an initiator component is generally added to the water phase of the HIPE emulsions and can be any conventional water-soluble free radical initiator. Materials of this type include peroxygen compounds such as sodium, potassium and ammonium persulfates, baprylyl peroxide, benzoyl peroxide, hydrogen peroxide, cumene hydroperoxides, tertiary butyl diperphthalate, tertiary butyl perbenzoate, sodium peracetate, sodium percarbonate and the like. Conventional redox initiator systems can also be utilized. Such systems are formed by combining the foregoing peroxygen compounds with reducing agents such as sodium bisulfite, L-ascorbic acid or ferrous salts.

The initiator material can comprise up to about 5 mole percent based on the total moles of polymerizable monomers present in the oil phase. More preferably, the initiator comprises from about 0.001 to 0.5 mole percent based on the total moles of polymerizable monomers in the oil phase. When used in the water-phase, such initiator concentrations can be realized by adding initiator to the water phase to the extent of from about 0.02% to 0.4%, more preferably from about 0.1% to 0.2% by weight of the water phase.

Via a process described more fully hereinafter, the oil and water phases as hereinbefore described are combined under agitation to form an emulsion in the form of a stable foam. This HIPE foam is then subjected to polymerization conditions which are sufficient and suitable to bring about polymerization of the monomers in the oil phase and to thereby form a solid cellular foam structure.

The chemical nature, makeup and morphology of the polymer material which forms the preferred storage/redistribution component foam structures herein is determined by both the type and concentration of the monomers, comonomers and crosslinkers utilized in the HIPE emulsion and by the emulsion polymerization conditions employed. Such polymeric material will generally be non-swellable in aqueous liquids in that the material itself does not significantly plasticize or imbibe aqueous liquids it contacts. However, no matter what the particular monomeric makeup, molecular weight or morphology of the polymer material might be, the resulting preferred polymeric material will generally be viscoelastic in character. Thus the polymer of the preferred storage/redistribution component foam structures herein will possess both viscous, i.e., fluid-like, properties and elastic, i.e., spring-like, properties. It is important that the polymeric material which forms the cellular foam structure have physical, rheological, and morphological attributes which, under conditions of use, impart suitable flexibility, resistance to compression deflection, and dimensional stability to the absorbent foam material.

The cross-linked polymer material that forms the preferred storage/redistribution component absorbent foam structures herein will preferably be substantially free of polar functional groups on its polymeric structure. Thus, immediately after the polymerization step, the polymer forming the foam structure surfaces of such preferred absorbent foams will normally be relatively hydrophobic in character. Accordingly, preferred just-polymerized foams may need to be further treated to render the foam structure surfaces relatively more hydrophilic so that such foams can be used as absorbents for aqueous body fluids in the storage/redistribution component of the articles herein. Hydrophilization of the foam surfaces, if necessary, can generally be accomplished by treating the HIPE foam structures as polymerized with a hydrophilizing agent in a manner described more fully hereinafter.

Hydrophilizing agents are any materials which will enhance the water wettability of the polymeric surfaces with which they are contacted and onto which they are deposited. Hydrophilizing agents are well known in the art. Such known agents will generally include surfactant materials of the anionic, cationic or nonionic type. Hydrophilizing agents will generally be employed in liquid form, typically dissolved in water to form an aqueous hydrophilizing solution which is applied to the HIPE foam surfaces. In this manner, hydrophilizing agents can be adsorbed to the polymeric surfaces of the preferred HIPE foam structures in amounts suitable for rendering such surfaces substantially hydrophilic but without altering the desired flexibility and compression deflection characteristics of the foam. In preferred foams which have been treated with hydrophilizing agents, hydrophilizing agent is incorporated into the foam structure such that residual amounts of the agent which remains in the foam structure comprise at least about 0.05% by weight, more preferably from about 0.1% to 10% by weight of the foam.

One type of suitable hydrophilizing agent comprises mild, relatively non-irritating surfactants applied to the foam structure in amounts sufficient to provide residual surfactant in the foam to the extent of from about 0.5% to 5.0% by weight, more preferably from about 1% to 3% by weight, based on the weight of the foam. Such surfactants can include, for example, alkyl sulfates and alkylethoxylated sulfates of the type utilized in commercially marketed dishwashing liquids such as JOY LIQUID DETERGENT. Aqueous solutions of such surfactants are typically used to wash the HIPE foam structure, either after removal of the residual water phase material left from the foam polymerization operation or, more preferably, as part of the washing treatment that serves to remove this residual water phase material.

Yet another preferred type of hydrophilizing agent comprises hydratable, and preferably hygroscopic or deliquesent, water soluble inorganic salts. Such materials include, for example, toxicologically acceptable calcium and magnesium salts. Materials of this type and their use in conjunction with water-insoluble surfactants as foam hydrophilizing agents are described in greater detail in the U.S. patent application of Thomas A. DesMarais having Ser. No. 07/743,951, concurrently filed herewith and incorporated herein by reference. Preferred salts of this type include the calcium and magnesium halides such as calcium chloride which, as noted hereinafter, may also be employed as the electrolyte in the water phase of the HIPE emulsions used to prepare preferred storage/redistribution component absorbent foams.

Hydrophilizing agents in the form of hydratable inorganic salts can easily be incorporated into the storage/redistribution component absorbent foams herein by treating the foams with aqueous solutions of such salts. As with surfactant hydrophilizing agents, solutions of hydratable inorganic salts can generally be used to treat and hydrophilize hydrophobic foams after completion of, or as part of, the process of removing the residual water phase from the just-polymerized foams. Contact of foams with such solutions is preferably used to uniformly deposit hydratable inorganic salts such as calcium chloride in residual amounts which range from about 0.1% to 7% by weight of the foam.

Hydrophilizing treatment of those of the preferred storage/redistribution component foam structures which are relatively hydrophobic as polymerized will typically be carried out to the extent that is necessary and sufficient to impart suitable hydrophilicity to the preferred HIPE storage component foams of the present invention. Some foams of the preferred HIPE emulsion type, however, may be suitably hydrophilic as prepared and thus may need no additional treatment with hydrophilizing agents. In particular, such preferred HIPE foams may be those wherein sorbitan fatty acid esters are used as emulsifiers added to the oil phase and calcium chloride is used as an electrolyte in the water phase of the HIPE emulsion foam precursors. In that instance, residual water-phase liquid held within the foams after polymerization may contain or deposit sufficient amounts of calcium chloride to render the residual-emulsifier-containing internal foam surfaces suitably hydrophilic even after the polymerized-emulsion foams have been dewatered.

V) Absorbent Foam Preparation Methods

The absorbent foam materials used in the storage/redistribution component of the absorbent articles herein can be prepared using any suitable polymerization and post-polymerization process steps and using any suitable combination of monomeric materials, so long as hydrophilic foams result which have the hereinbefore described essential, and if desired preferred, fluid handling, structural and mechanical characteristics. As noted, a preferred method of realizing polymeric foams having the requisite fluid handling properties and the desired structural and mechanical characteristics, involves the polymerization of High Internal Phase Emulsions (HIPEs). Preparation of absorbent storage/redistribution component foams using this preferred procedure will thus be described to illustrate how foams of the type envisioned herein can be made.

This preferred foam preparation method involves the steps of, A) forming a stable high internal phase emulsion (HIPE), B) thereafter polymerizing this stable emulsion under conditions suitable for forming a solid polymeric foam structure, C) washing and, if necessary, hydrophilizing the solid polymeric foam structure by treating the structure with water and/or liquid-form hydrophilizing agents to remove the original residual water phase from the polymeric foam structure and to deposit any needed hydrophilizing agent, and D) thereafter dewatering this polymeric foam structure to the extent necessary to render the foam material useful as a storage component absorbent for aqueous body fluids. Each of these basic process steps is described in greater detail as follows:

A) Formation of HIPE Emulsion

The HIPE emulsion precursor to the preferred foam absorbent materials herein can be formed by combining an oil phase as hereinbefore described with a water phase also as hereinbefore described. The weight ratio of the water phase to the oil phase and such a combination will generally range form about 12:1 to 100:1, more preferably from about 20:1 to 70:1.

The oil phase used to form the HIPE emulsions herein will contain the hereinbefore specified essential components such as the requisite monomers, comonomers, cross-linkers and emulsifiers. The oil phase may also contain optional components such as solvents and polymerization initiators. The water phase used to form the HIPE emulsions herein will contain the hereinbefore specified electrolyte as an essential component and may also contain optional components such as water-soluble emulsifiers, and/or polymerization initiators.

The HIPE emulsion can be formed from the combined oil and water phase by subjecting this combination of phases to shear agitation. Shear agitation is generally applied to the extent and for a time period necessary to form a stable emulsion from the combined oil and water phases. Such a process may be conducted in either batchwise or continuous fashion and is generally carried out under conditions suitable for forming an emulsion wherein the oil phase droplets are dispersed to such an extent that the polymerized foam which is eventually formed from the emulsion will have the requisite pore volume and other structural characteristics. Emulsification of the oil and water phase combination will frequently involve the use of a mixing or agitation device such as a pin impeller.

One preferred method of forming HIPE emulsions which can be employed herein involves a continuous process for combining and emulsifying the requisite oil and water phases. In such a process, a liquid stream comprising the oil phase as hereinbefore described is formed and provided at a flow rate ranging from about 0.08 to 1.5 ml/sec. Concurrently, a liquid stream comprising the water phase as hereinbefore described is also formed and provided at a flow rate ranging from about 4 to 50 ml/sec. At flow rates within the foregoing ranges, these two streams are then combined in a suitable mixing chamber or zone in a manner such that the requisite water to oil phase weight ratios as hereinbefore set forth are approached, reached and maintained.

In the mixing chamber or zone, the combined streams are generally subjected to shear agitation as provided, for example, by a pin impeller of suitable configuration and dimensions. Shear will typically be applied to the extent of from about 1000 to 4000 sec.$^{-1}$. Residence times in the mixing chamber will frequently range from about 5 to 30 seconds. Once formed, the stable HIPE emulsion in liquid form can be withdrawn from the mixing chamber or zone at a flow rate from about 4 to 52 ml/sec.

This preferred method for forming useful HIPE emulsions via a continuous process is described in greater detail in the U.S. patent application of Thomas A. DesMarais, Stephen T. Dick and Thomas M. Shiveley having Ser. No. 07/743,947. This application, which is concurrently filed herewith, is incorporated herein by reference.

B) Polymerization of the HIPE Emulsion

The HIPE emulsion, formed as described hereinbefore, will generally be placed in a suitable reaction vessel, container or region to be polymerized. In one embodiment herein, the reaction vessel comprises a tub constructed of polyethylene from which the eventually polymerized solid foam material can be easily removed for further processing after polymerization has been carried out to the extent desired.

Polymerization conditions to which the HIPE emulsion will be subjected will vary depending upon the monomeric and other makeup of the oil and water phases of the emulsion and the type and amounts of polymerization initiators utilized. Frequently, however, polymerization conditions will comprise maintenance of the HIPE emulsion at elevated temperatures of from about 55° C. to 90° C., more preferably from about 60° C. to 66° C., for a time period ranging from about 4 to 24 hours, more preferably from about 4 to 12 hours.

C) Washing and Hydrophilizing of the HIPE Foam

The solid HIPE foam which is formed upon completion of the hereinbefore described polymerization step will generally be a flexible, open-cell porous structure having its cells filled with the residual water phase material which was used to prepare the HIPE emulsion prior to polymerization. This residual water phase material, which generally comprises an aqueous solution of electrolyte, residual emulsifier, and polymerization initiator, should be removed from the foam structure at this point prior to further processing and use of the foam.

Removal of the original water phase material will usually be carried out by compressing the foam structure to squeeze out residual liquid and/or by washing the foam structure with water or other aqueous washing solutions. Frequently several compressing and washing steps, e.g., 2 cycles, will be utilized.

After the original water phase material has been removed from the foam structure to the extent required, the HIPE foam may need to be treated, i.e., by continued washing, with an aqueous solution of a suitable hydrophilizing agent. Hydrophilizing agents which may be employed are listed hereinbefore. As noted, treatment of the HIPE foam structure with the hydrophilizing agent solution continues, if necessary, until the desired amount of hydrophilizing agent has been incorporated and until the foam exhibits a desired adhesion tension value for any aqueous liquid absorbate of choice.

D) Foam Dewatering

After the HIPE foam has been treated to the extent necessary to render the eventually dried foam suitably hydrophilic, the foam will generally be dewatered prior to being cut or otherwise made ready for use as an absorbent structure in the storage/redistribution component of an absorbent article. Dewatering can be brought about by compressing the foam to squeeze out residual water, by subjecting the foam, or the water therein, to elevated temperatures, e.g., to temperatures from about 60° C. to 200° C. or to microwave treatment, or by a combination of both compressing and water heating techniques. The dewatering step of HIPE foam processing will generally be carried out until the HIPE foam ready for use is as dry as practical. Frequently such compression dewatered foams will have a water (moisture) content of from about 50% to 500%, more preferably from about 50% to 200%, by weight on a dry weight basis. Subsequently, heated foams can be dried to a moisture content of from about 5% to 40%, more preferably from about 5% to 15% by weight.

ABSORBENT CORE PREPARATION-RELATIONSHIP OF ACQUISITION/DISTRIBUTION AND STORAGE/REDISTRIBUTION COMPONENTS

As noted, both the upper acquisition/distribution component and the fluid storage/redistribution component are arranged into an absorbent core which is positioned between the topsheet and backing sheet to form the absorbent articles herein. There is no particular criticality with respect to the positional relationship of the acquisition/distribution component and the fluid storage/redistribution component within the absorbent core so long as these components are in effective fluid communication with each other and so long as each component is large enough to effectively hold and/or transport the amount of aqueous body fluid that is expected to be discharged into the absorbent article.

As previously indicated, the most preferred relationship between the fluid acquisition/distribution component and the fluid storage/redistribution component within the absorbent core of the articles herein is to place these components in a layered configuration. In such a layered configuration, the fluid acquisition/distribution component comprises an upper layer which overlies a subjacent fluid storage/redistribution component in the form of a lower layer. It should be understood that for purposes of this invention these two types of layers refer merely to the upper and lower zones of the absorbent core and are not necessarily limited to single, or even physically separate, layers or sheets of material. Both the fluid acquisition/distribution zone, e.g., upper layer, and the fluid storage/redistribution zone, e.g., lower layer, may simply comprise regions of different characteristics within the same material or may comprise laminates or combinations of several sheets or webs or polymeric foams of the requisite type of materials as hereinbefore described. Thus, as used herein, the term "layer" includes the terms "layers" and "layered". For purposes of this invention, it should also be understood that the term "upper" refers to the layer of the absorbent core which is relatively nearer to the article top sheet; conversely, the term "lower" refers to the layer "lower" refers to the layer of the absorbent core which is relatively nearer the article backing sheet.

In layered structures, it is, of course, desirable for economic reasons to employ as little absorbent material as possible in each component of the absorbent core consistent with the need to provide adequate absorption of body fluid with minimal leakage of such fluid from the article. The interaction of the particular types of acquisition/distribution and storage/redistribution layers utilized in the preferred layered articles of this invention results in especially efficient handling of discharged fluid and this in turn permits utilization of relatively small amounts of absorbent material in each layer. In the preferred absorbent articles of the present invention, the upper fluid acquisition/distribution layer will preferably comprise from about 1 to 25 grams, more preferably from about 2 to 20 grams of fluid absorbing material. The lower fluid storage/redistribution layer of the preferred absorbent articles herein will generally comprise from about 2 to 20 grams, more preferably from about 3 to 17 grams of foam-based absorbent material. The weight ratio of the acquisition/distribution layer to the storage/redistribution layer will generally range from about 1:4 to 5:1, more preferably from about 1:3 to 4:1, in the preferred absorbent articles herein.

In preferred invention embodiments, the acquisition/distribution layer of the absorbent core will be placed in a specific positional relationship with respect to the article topsheet and the storage/redistribution layer of the absorbent core. More particularly, the acquisition/distribution layer of the core is preferably positioned so that it is effectively located to acquire discharged body fluid and transport such fluid to other regions of the core. Thus the acquisition/distribution layer should preferably encompass the vicinity of the point of discharge of body fluids. These areas would include the crotch area and, preferably for articles to be worn by males, also the region where urination discharges occur in the front of the diaper. For a diaper, the front of the absorbent articles herein means the portion of the absorbent article which is intended to be placed on the front of the wearer. Additionally, for male wearers, it is desirable for the acquisition/distribution layer to extend to near the front waist area of the wearer to effectively acquire the relatively high fluid load that occurs in the front of diapers for male wearers, and to compensate for directional variations of the discharges. The corresponding absorbent article regions will vary depending upon the design and fit of the absorbent article.

For diaper executions, the acquisition/distribution layer of the core is preferably positioned relative to an elongated topsheet and/or the storage/redistribution layer such that the acquisition/distribution layer is of sufficient length to extend to areas corresponding at least to about 50%, preferably 75%, of the length of the topsheet and/or storage/redistribution layer. The acquisition/distribution layer should have a width sufficient to acquire gushes of body fluids and to prevent direct discharge of fluid onto the storage/redistribution layer. Generally, for diapers, the width of the acquisition/distribution layer will be at least about 5 cm, preferably at least about 6 cm.

For purposes of determining such preferred acquisition/distribution layer positioning as hereinbefore described, the length of the absorbent article will be taken as the normal longest longitudinal dimension of the elongated article backing sheet. This normal longest dimension of the elongated backing sheet can be defined with respect to the article as it is applied to the wearer. When worn, the opposing ends of the back sheet are fastened together so that these joined ends form a circle around the wearer's waist. The normal length of the backing sheet will thus be the length of the line running through the back sheet from a) the point on the edge of the back sheet at the middle of the wearer's back waist, through the crotch, to b) the point on the opposite edge of the backing sheet at the middle of the wearer s front waist. The size and shape of the topsheet will generally correspond substantially to the back sheet.

In the usual instance, it will be the storage/redistribution layer of the preferred absorbent cores which generally defines the shape of the absorbent article and the normal length of the elongated article topsheet will be approached by the longest longitudinal dimension of the storage/redistribution layer of the core. However, in some applications (e.g., adult incontinence articles) wherein bulk reduction or minimum cost are important, the storage/redistribution layer would not take on the general shape of the diaper or incontinence structure. Rather the storage/redistribution layer would be generally located to cover only the genital region of the wearer and a reasonable area proximate to the genital area. In this instance both the fluid acquisition/distribution layer and the storage/redistribution layer would be located toward the front of the article as defined by the topsheet such that the acquisition/distribution and storage/redistribution layers would typically be found in the front two-thirds of the article length.

As noted, the relative size of the acquisition/distribution layer and the fluid storage/redistribution layer in preferred articles can vary widely. Preferably, however, the acquisition/distribution layer of the preferred absorbent core configuration will have a smaller surface area (in a planar unfolded configuration) than the storage/redistribution layer and, in fact, can have a surface area that is substantially smaller than that of the fluid storage/redistribution layer. Frequently, the surface area of the acquisition/distribution layer will range from about 15% to about 95%, preferably from about 30% to about 85%, more preferably from about 30% to about 75%, of the surface area of the storage/redistribution layer.

The acquisition/distribution layer can be of any desired shape consistent with comfortable fit and the sizing limitations discussed above. These shapes include, for example, circular, rectangular, trapezoidal or oblong, e.g., hourglass-shaped, dog-bone-shaped, half dog bone shaped, oval or irregularly shaped. The acquisition/distribution layer can be of similar shape or differing shape than the storage/redistribution layer. The storage/redistribution layer of the preferred absorbent core configuration can also be of any desired shape consistent with comfortable fit including, for example, circular, rectangular, trapezoidal or oblong, e.g., hourglass-shaped, dog-bone-shaped, half dog bone shaped, oval or irregularly shaped. The storage/redistribution layer need not be physically separated from the acquisition/distribution layer or completely unattached from the storage/redistribution layer.

Figure 2:
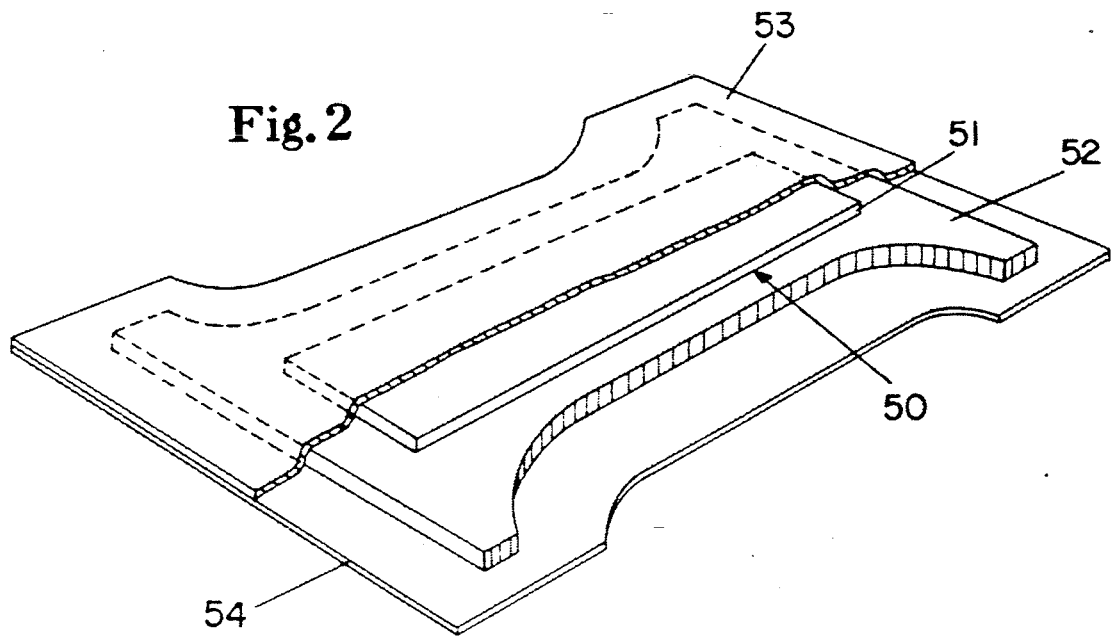
FIG. 2 of the drawings is a cutaway depiction of a disposable diaper which utilizes an absorbent foam material as an hourglass-shaped fluid storage/redistribution component underlying a rectangular fibrous fluid acquisition/distribution component in an absorbent diaper core of dual-layer configuration.

A preferred disposable diaper embodiment of this invention is illustrated by FIG. 2 of the drawings. Such a diaper includes an absorbent core, 50, comprising an upper fluid acquisition layer, 51, and an underlying fluid storage/redistribution layer, 52, comprising a foam absorbent structure. A topsheet, 53, is superposed and co-extensive with one face of the core, and a liquid impervious backsheet, 54, is superposed and coextensive with the face of the core opposite the face covered by the topsheet. The backsheet most preferably has a width greater than that of the core thereby providing side marginal portions of the backsheet which extend beyond the core. The diaper is preferably constructed as shown, in an hourglass configuration.

Figure 3:
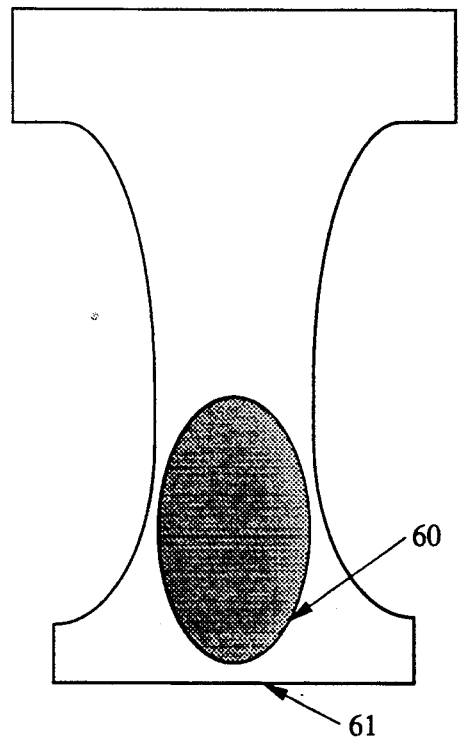
FIGS. 3 and 4 of the drawings represent, respectively, a top view and a side view of an alternative absorbent core configuration wherein a fluid acquisition/distribution component is surrounded by a foam-based fluid storage/redistribution component.
Figure 4:
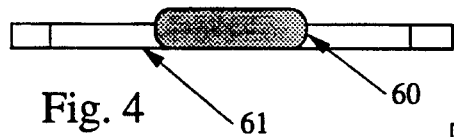

As noted, the acquisition/distribution component and the storage/redistribution component of the absorbent core need not be arranged in a layered relationship at all in the articles herein. An alternative absorbent core configuration which is not layered is shown in FIGS. 3 and 4. In FIGS. 3 and 4, the fluid acquisition/distribution component comprises an insert 60 of a low density, resilient composite material which is imbedded in and surrounded by a foam-based fluid storage/redistribution component 61. The acquisition/distribution composite insert 60 is positioned at the point within the absorbent core wherein it will receive body fluid discharged by the wearer of the absorbent article.

Figure 5:
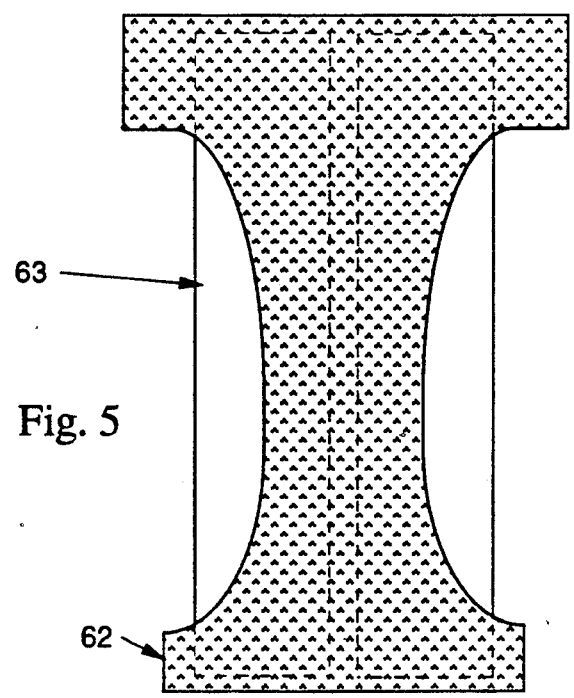
FIGS. 5 and 6 of the drawings represent, respectively, a top view and a side view of another alternative absorbent core configuration which employs a fluid storage/redistribution component in the form of discrete strips of foam material.
Figure 6:
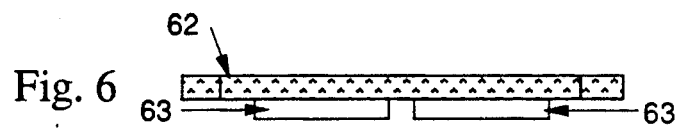

FIGS. 5 and 6 show another alternative absorbent core configuration. In this configuration, a cellulosic-based fibrous material in the form of an hourglass-shaped sheet 62 is positioned on top of a foam-based fluid storage/redistribution component which comprises two parallel generally rectangular strips, 63.

Figure 7:
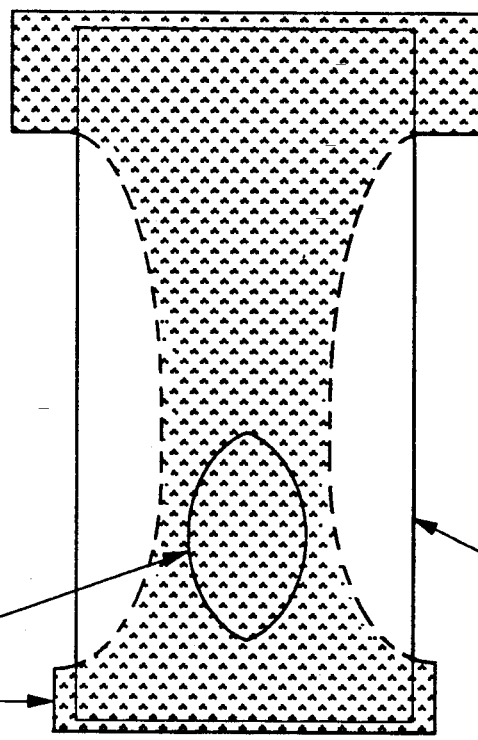
FIGS. 7 and 8 of the drawings represent, respectively, a top view and a side view of yet another alternative core configuration wherein the fluid storage/redistribution component overlies a subjacent fluid acquisition/distribution component.
Figure 8:
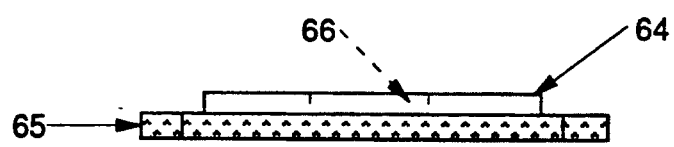

FIGS. 7 and 8 show yet another alternative absorbent core configuration wherein the foam-based fluid storage/redistribution component comprises a generally rectangularly-shaped top layer 64 which is placed over an underlying hourglass-shaped fluid acquisition/distribution lower layer 65. The fluid storage/redistribution layer contains a fluid acquisition aperture 66 through which body fluid is discharged so as to impinge on the subjacent acquisition/distribution lower layer 65.

TEST METHODS

In describing the present invention, a number of fluid handling, structural and mechanical characteristics of materials or structures used in the two absorbent core components of the absorbent articles herein are set forth. In some instances, procedures for determining and measuring certain of these characteristics are referenced from other patents or publications. In the remaining instances, such characteristics can be determined and measured using the following test fluids and test methods.

I) Test Fluids and Structure Sample Preparation

A) Test Fluid—Synthetic Urine

Several of the measurements described in the tests herein involve the use of a test fluid such as synthetic urine, ethanol, or isopropanol. The synthetic urine utilized in a number of the tests described hereinafter is made from a commercially available synthetic urine manufactured by Jayco Pharmaceuticals (Mechanicsburg, Pa., 17055). This Jayco synthetic urine made from the preparation comprises KCl, 0.2%; $Na_2SO_4$, 0.2%; $NH_4H_2PO_4$, 0.085%; $(NH_4)_2HPO_4$, 0.015%; $CaCl_2*2H_2O$, 0.025%; and $MgCl_2*6H_2O$, 0.05% (Percentage by weight). The synthetic urine samples are prepared according to the label instructions using distilled water. To aid dissolution, the Jayco salt mixture is slowly added to the water. The sample is filtered if necessary to remove any particulates. Any unused synthetic urine is discarded after one week. To improve visibility of the fluid, 5 drops of blue food color can be added per liter of synthetic urine solution. The Jayco synthetic urine utilized has a surface tension of $65\pm 5$ dynes/cm.

B) Absorbent Structure Sample Preparation

A number of the following tests involve the preparation and testing of absorbent structure, e.g., foam samples, of a particular specified size. Unless otherwise specified, absorbent structure samples of the requisite size should be cut from larger blocks of the same material using a sharp reciprocating knife saw. Use of this or equivalent type of sharp cutting device serves to substantially eliminate sample edge flaws and edge densification effects which could have adverse impact on the accuracy of certain of the measurements made in carrying out the several test procedures hereinafter set forth.

Sample size specification will also generally include a dimension for sample caliper or thickness. Caliper or thickness measurements for purposes of the present invention should be made when the absorbent structure sample is under a confining pressure of 0.05 psi (350 Pa).

II) Determination of Fluid Handling Characteristics of the Acquisition/Distribution Layer

A) Fluid Acquisition Rate

The rate at which a particular type of fiber-based or foam-based absorbent material will accept fluid into its internal structure can be determined for purposes of the present invention by a Fluid Acquisition Rate test. In such a test, a specified amount of test liquid is introduced onto the top surface of the structure being tested, and the amount of time required for all of this test liquid to be absorbed into the structure is measured.

The setup for the Fluid Acquisition Rate test involves the preparation of a $4'\times 4'$ (10.16 cm $\times$ 10.16 cm) piece of absorbent structure material of any suitable caliper. This test sample is weighed and is placed on top of a $5'\times 5'$ (12.7 cm $\times$ 12.7 cm) Plexiglas plate. Placed on top of the absorbent structure is a Strike Through Device which comprises a $4'\times 4'$ (10.16 cm $\times$ 10.16 cm) Plexiglas plate having a cylindrical hole $1'$ (2.54 cm) in diameter $\times \frac{3}{4}'$ (1.9 cm) deep which serves as a load cell. The load cell is fitted with electric sensors which detect the presence of test liquid in the load cell. The sensors are connected to a timer such that the amount of time liquid remains in the load cell can be automatically determined. The device which positions the sensor in the load cell limits the cross-sectional area across which test liquid flows to about 0.33 in$^2$ (2.13 cm$^2$). Weights are placed on top of the Strike Through Device such that the absorbent structure sample being tested is maintained under a confining pressure of 0.2 psi (1.43 kPa).

An amount of JAYCO synthetic urine test liquid equal to two times (2X) the weight of the absorbent structure test sample is placed in a dispensing funnel which is positioned above the load cell of the Strike Through Device. At time zero, the timer is started, and the test liquid is dispensed from the dispensing funnel into the load cell of the Strike Through Device. (When the valve on the dispersing funnel is fully open, fluid flows into the load cell at the rate of about 11 mL/sec.) The timer is stopped when the electric sensors detect that all of the test liquid has been drained from the load cell and absorbed into the test structure.

The amount of time taken for the first aliquot of test liquid to be absorbed into the test structure is taken as the initial Fluid Acquisition Rate. Subsequent 2X aliquots of test liquid can be fed into the load cell at intervals of 2-3 minutes. In this manner, Fluid Acquisition Rate as a function of structure fluid loading can also be determined.

B) Vertical Wicking Height

Vertical wicking characteristics of material suitable for use as or in the fluid acquisition/distribution component of the articles herein can be determined by the Vertical Wicking Height test. In such a test, a 10'×1' (25.4 cm×2.54 cm) strip of an absorbent structure test sample of any suitable caliper (e.g., 0.15 in [0.38 cm] for fiber-based structures; 0.25 in [0.13 cm] for foam-based structures) is used. This test strip is positioned vertically over a reservoir of a JAYCO synthetic urine test liquid. At time zero, the test strip is lowered into the reservoir to a point on the strip marked as the zero point. After 30 minutes, the level to which test liquid has wicked above the zero point on the test strip is measured. This distance is then taken as the 30 minute Vertical Wicking Height.

III) Determination of Fluid Handling Characteristics of the Absorbent Foam Structures of the Fluid Storage/Redistribution Component

A) Absorbent Caoacitv of the Foam

Both free absorbent capacity and absorbent capacity under pressure of foam structures can be determined by a gravimetric analytical technique using synthetic urine as the fluid for which absorbent capacity of the foam is to be calculated.

1) Principle of the Absorbent Caoacitv Testing

In this test, a foam sample is saturated with synthetic urine test liquid to measure the no-load or free absorbent capacity of the foam sample. Pressure is then applied in various increments to determine absorbent capacity under load. This absorbent capacity under pressure is measured after the foam sample has been held in a compressed state for a fixed amount of time.

2) Scope of Testing

This test measures the absorbent capacity of a foam sample under pressures of interest, namely from 0 to 1.0 pound per square inch (psi) (0 to 6.9 kPa), and at the temperature of interest, i.e., 99° F. (37° C.).

3) Equipment

Screen, 25 mesh, 8 cm in diameter; crystallizing dish, 15 cm diameter×7.5 cm high; beaker, 50 mL; analytical balance; dial-type gauge, fitted with a foot at least 1 in$^2$ (6.5 cm$^2$) and capable of measuring to 0.001 inch (0.025 mm), e.g., Ames model 482 (Ames Co., Waltham, Mass.) or Ono-Sokki model EG-225, Ono-Sokki Co., Ltd., Japan); weights for the dial-type gauge capable of producing pressures of 0.2, 0.74, and 1.0 psi (1.4, 5.1, and 6.9 kPa).

4) Materials

JAYCO synthetic urine; foam samples.

5) Procedure i) The equipment and materials hereinbefore described are equilibrated in a constant temperature room heated to 99° F. (37° C). Measurements are also performed in this room.

ii) Foam samples are cut into 1 in$^2$ (6.5 cm$^2$)×0.3 in (0.8 cm) thick cylinders or equivalent. These samples are weighed to provide an average dry weight (DW).

iii) Free Absorbent Capacity (FAC) of each foam sample is determined as follows:
  a) The foam sample is immersed into the synthetic urine in the crystallizing dish and allowed to saturate. The sample may be squeezed a few times to expel air.
  b) The foam is removed without squeezing fluid out of it. Excess fluid is allowed to drip off of the sample in the flat position for about 30 seconds, and then the wet sample is weighed.
  c) Steps a) and b) are repeated two more times and an average wet weight (WW) is calculated.
  d) The Free Absorbent Capacity (FAC, g/g is calculated as $$FAC = \text{weight synthetic urine in saturated foam/dry weight foam}$$
$$= [WW(g) - DW(g)]/DW(g)$$

iv) Absorbent Capacity Under Pressure (Pressure Desorption) for each foam sample is determined as follows:
  a) The 50 mL beaker, with the screen on top of it, is positioned under the center of the foot of the dial-type gauge, with the foot resting on the screen.
  b) The saturated sample is placed on top of the screen, making sure the sample is over the center of the beaker, and the dial-type gauge is positioned to apply confining pressure on the foam sample.
  c) Weights are placed on the gauge to apply 0.2 psi (1.4 kPa) of pressure on the sample.
  d) After 15 minutes, the foam sample is weighed (WW,0.2).
  e) The same sample is resaturated, and then steps a)–d) are repeated except the 0.74 and 1.0 psi are used to determine WW,0.74 and WW,1.0.
  f) Using new samples, steps a)–e) are repeated two more times to determine average wet weights after the samples are held under the different pressures.
  g) Absorbent capacities under pressure (X-load, g/g are calculated as shown. (X-load under a given pressure is the weight synthetic urine in wet foam/dry weight foam.)

Capacity under 0.2 psi
$X,0.2 (g/g) = [WW,0.2 (g) - DW(g)]/DW(g)$

Capacity under 0.74 psi
$X,0.74 (g/g) = [WW,0.74 (g) - DW(g)]/DW(g)$

Capacity under 1.0 psi

-continued
$$X,1.0 \text{ (g/g)} = [WW,1.0 \text{ (g)} - DW \text{ (g)}]/DW \text{ (g)}$$

Absorbent capacity values in ml of synthetic urine per gram of dry foam can be obtained by dividing the FAC and the X-load values by the specific gravity of the Jayco synthetic urine which is approximately 1 g/ml.

B) Vertical Wicking Rate and Vertical Wicking Absorbent Capacity of the Foam Vertical wicking rate and vertical wicking absorbent capacity are measures of the ability of a dry foam to wick fluid vertically from a reservoir. The time required for the fluid front to wick through a 5 cm vertical length of a strip of foam is measured to give a vertical wicking rate. After fluid wicks to its equilibrium height, the amount of fluid held by the foam strip at a particular vertical wicking height (e.g., 4.5 inches or 11.4 cm) is determined to give a vertical wicking absorbent capacity.

Jayco synthetic urine colored with blue food coloring is used in the following methods to determine vertical wicking rate and vertical wicking absorbent capacity. In this test procedure, the materials are equilibrated at 37° C. and the test is performed at the same temperature.

1) Sample Preparation
   i) A strip of foam approximately 25 cm×2.0 cm×0.8 cm is cut from a parent sample.
   ii) A fluid reservoir is placed on top of a lab jack and the foam sample is clamped at one end so that it is suspended vertically over the fluid reservoir.
   iii) A ruler is clamped next to the foam sample so that the bottom (0 cm) of the ruler is about 1-2 mm above the bottom of the foam sample.
   iv) The fluid reservoir is filled about ¾ full with the dyed synthetic urine solution.

2) Vertical Wicking Rate
   i) The reservoir is raised up to the bottom of the foam sample with the lab jack. A timer is started as soon as the fluid touches the bottom of the foam sample.
   ii) The reservoir is immediately raised until the liquid just touches the bottom of the ruler.
   iii) The time it takes the fluid front to reach 5 cm is recorded.
   iv) The foam is allowed to wick until it reaches equilibrium (e.g., about 18 hours). The lab jack may need to be adjusted to keep 1-2 mm of the sample immersed, and the sample should be shielded to prevent evaporation.

3) Absorbent Capacity (ml/g) per Vertical Length of Foam
   i) The foam sample is removed and placed on a non-absorbent surface.
   ii) The sample is immediately cut into separate 1 inch (2.54 cm) pieces using a tool sharp enough not to compress the foam sample, and each such piece is weighed.
   iii) The excess fluid is squeezed out of each piece, and each piece is placed on an absorbent towel.
   iv) Each piece is allowed to dry complete
   v) Each dry piece is then weighed and an absorbent capacity for each piece is calculated based on the difference between the wet and dry weights. For purposes of the present invention, the absorbent capacity of the one-inch segment which represents 4.5 inches (11.4 cm) of wicking height is the parameter most desirably determined.

C) Adhesion Tension Characteristics of the Foam

The adhesion tension exhibited by hydrophilized foam samples which imbibe test fluids via capillary suction is the product of the surface tension, $\gamma$, of the test fluid times the cosine of the contact angle, $\Theta$, exhibited by the test fluid in contact with the interior surfaces of the foam sample. Adhesion tension can be determined experimentally by measuring the equilibrium weight uptake by capillary suction exhibited by two test samples of the same foam using two different test liquids. In the first step of such a procedure, specific surface area of the foam sample is determined using ethanol as the test fluid as described hereinafter in the Specific Surface Area discussion of this TEST METHODS section.

The capillary suction uptake procedure is then repeated in identical manner to the ethanol procedure except that JAYCO synthetic urine is used as the test fluid and the test is carried out at 37° C. Contact angle of the synthetic urine can then be calculated as follows from the known specific surface area and the synthetic urine uptake data:

$$\cos\theta_U = \frac{M_U G L_N}{M_N \gamma_U S_c}$$

where $\Theta_U$=contact angle of Jayco synthetic urine in degrees; $M_U$=mass of liquid uptake of Jayco synthetic urine in gms; G=gravitational constant which is 980 cm/sec$^2$; $M_N$=mass of dry foam sample in gm; $\gamma_U$=surface tension of JAYCO urine which is ~65 dynes/cm; $S_c$=specific surface area of the foam sample in cm$^2$/gm as determined by the ethanol uptake procedure; and $L_n$=length of the foam sample in cm.

When a surfactant is present (on the foam sample surfaces and/or in the advancing test liquid), characterization of the advancing liquid front is defined by applying the adhesion tension (AT) equation:

$$AT = \frac{M_T G L_N}{M_N S_c}$$

wherein $M_T$ is the mass of the test liquid taken up by the foam sample, and G, $L_N$, $M_N$, and $S_c$ are as hereinbefore defined. [See Hodgson and Berg, J. Coll. Int. Sci.. 121(1), 1988, pp 22-31]

In determining adhesion tension for any given test liquid, no assumption is made of the numerical value of the surface tension at any point in time so that possible changes in surfactant concentration on the sample surfaces and/or in the advancing liquid during wicking are immaterial. The experimental value of adhesion tension ($\gamma \cos \theta$) is especially useful when viewed as a percentage of the maximum adhesion tension which is the surface tension of the test liquid (e.g., the maximum adhesion tension using JAYCO synthetic urine would be [65±5] [cos 0°]=65±5 dynes/cm.

IV) Determination of Structural Characteristics of the Absorbent Foam Structures of the Fluid Storage/Redistribution Component

A) Available Pore Volume of the Foam

A procedure for determining available pore volume involves the measurement of the amount of isopropanol (flash point 12° C.) which can be introduced into the structure of an absorbent foam sample. Equipment and materials used in making such a measurement are equilibrated at 22±2° C. Measurements are also performed at this temperature.

Dry foam samples are cut into 1 in² (6.5 cm²)×0.3 inch (0.8 cm) thick cylinders or the equivalent. Such cylindrical samples can be prepared by using a sharp punch 1.13 inches (2.87 cm) in diameter on a 0.3 inch (0.8 cm) sheet of foam. These dry foam samples are each weighed to determine a dry weight (dw). Three of such samples are weighed to determine an average dry weight (DW).

The Measured Free Capacity (MFC) of these samples is then determined by the following steps:
1) The foam samples are immersed in the isopropanol in a crystallizing dish and allowed to saturate. At this point, the sample may be squeezed a few times to expel air.
2) Each sample is removed without squeezing isopropanol out of it. Excess fluid is allowed to drip off of the sample in the flat position for about 30 seconds. Each sample is then weighed wet to determine a wet weight (ww).
3) Steps 1) and 2) are repeated two more times and an average wet weight (WW) is calculated.

Measured Free Capacity (MFC, g/g) is the weight of isopropanol in the saturated foam per unit mass of dry foam. MFC is calculated according to the formula $$MFC = \frac{[WW(g) - DW(g)]}{DW(g)}$$

Available pore volume is then calculated by dividing the MFC of the foam for isopropanol by the density of isopropanol which is 0.785 g/ml. This gives an available pore volume for the foam in ml/g.

B) Capillary Suction Specific Surface Area of the Foam

Capillary Suction Specific surface area of the foam absorbents useful in the fluid storage/redistribution component herein can be determined from the equilibrium weight uptake of a test liquid of known low surface tension. In this instance, absolute ethanol (flash point is 10° C.) is used.

To conduct the test, a tared foam sample strip of suitable dimensions (e.g., 25 cm long×2 cm wide×0.8 cm thick) is equilibrated at 22±2° C., is positioned vertically and at one end is immersed 1-2 mm into a reservoir of the ethanol using a lab Jack. The ethanol is allowed to wick up the foam strip to its equilibrium height which should be less than the sample length. The ethanol-containing strip is then weighed while still touching the reservoir to determine the weight of total ethanol uptake. During this procedure the sample should be shielded, for example with a capped glass cylinder, to prevent ethanol evaporation.

Specific surface area of the foam sample can be calculated from the following formula:

$$S_c = \frac{M_e G L_n}{M_n \gamma_e}$$

where $S_c$=capillary suction specific surface area in cm²/gm; $M_e$=mass of liquid uptake of EtOH in gms; G=the gravitational constant which is 980 cm/sec²; $L_n$=total length of sample in cm; $M_n$=mass of dry sample in gm; and $\gamma_e$=surface tension of EtOH which is 22.3 dynes/cm. Values obtained can then be divided by 10000 cm²/m² to provide capillary suction specific surface area in m²/g.

C) Foam Density

One procedure which can be used to determine foam density is that described in ASTM Method No. D3574-86, Test A, which is designed primarily for the testing of urethane foams but which can also be utilized for measuring density of the preferred HIPE-type, storage/redistribution component absorbent foams of the present invention. In particular, density measurements made according to this ASTM procedure are carried out on foam samples which have been preconditioned in a certain manner as specified in that test.

Density is determined by measuring both the dry mass of a given foam sample and its volume at 22±2° C. Volume determination on larger foam samples are calculated from measurements of the sample dimensions made under no confining pressure. Dimensions of smaller foam samples may be measured using a dial-type gauge using a pressure on the dial foot of 350 Pa (0.05 psi).

Density is calculated as mass per unit volume. For purposes of this invention, density is generally expressed in terms of g/cm³.

V) Determination of Mechanical Characteristics of the Absorbent Foam Structures of the Fluid Storage/Redistribution Component A) Resistance to Compression Deflection of the Foam Resistance to compression deflection exhibited by the storage/redistribution component foam can be quantified for purposes of this invention by measuring the amount of strain (% caliper reduction) produced in a foam sample, which has been saturated with synthetic urine, after stress in the form of a 0.74 psi (5.1 kPa) confining pressure has been applied to the sample.

Testing to make such measurements can be carried out on foam samples prepared as hereinbefore described for the Available Pore Volume test. Such samples, the synthetic urine test fluid and equipment used to make measurements are all equilibrated in a constant temperature room heated to 99° F. (37° C). Measurements are also performed in this room.

The foam samples are placed in a crystallizing dish and saturated to their free absorbent capacity with Jayco synthetic urine. A given saturated sample to be tested is then placed on a 25 mesh screen over a beaker, and a dial-type gauge suitable for making caliper measurements is positioned on the sample. Any gauge fitted with a foot having a surface area of at least 1 in² (6.5 cm²) and capable of measuring caliper dimensions to 0.001 in (0.025 mm) can be employed. Examples of such gauges are an Ames model 482 (Ames Co.; Waltham, Mass.) or an Ono-Sokki model EG-225 (Ono-Sokki Co., Ltd.; Japan). Also utilized are weights which can be used with the dial gauge to produce a foot pressure on the foam sample of up to 1.0 psi (6.9 kPa).

The saturated foam sample on the screen is subjected to a confining pressure of 0.74 psi (5.1 kPa) for 15 minutes. At the end of this time, the dial gauge is used to measure the change in sample caliper which occurs as a consequence of the application of the confining pressure. From the initial and final caliper measurements, a percent strain induced can be calculated for the sample.

B) Flexibility of the Foam

Foam flexibility can be quantified by referencing a test procedure which is a modification of the ASTM D 3574-86, 3.3 test used to determine flexibility of cellular organic polymeric foam products. Such a modified test utilizes a foam sample which is 7×0.8.×0.8 cm and which has been saturated to its free absorbent capacity with Jayco synthetic urine at 37° C. It is important that the cutting process used to make these samples does not introduce edge defects in the foam strip. The synthetic urine-saturated foam strip is bent around a 0.8 cm diameter cylindrical mandrel at a uniform rate of 1 lap in 5 seconds until the ends of the strip meet. The foam is considered flexible if it does not tear or break during this test, i.e., if it passes one bending cycle.

C) Recovery From Compression Deflection of the Foam

To test recovery from compression deflection, foam samples similar to those prepared for the Available Pore Volume test hereinbefore described are used. Such samples are 0.8 cm thick cylinders having a cross-sectional circular area of 6.45 cm$^2$ (1 in$^2$). These foam samples may be tested in either the dry state or after they have been saturated to their free absorbent capacity with Jayco synthetic urine.

Using a dial-type gauge, a test sample, whether dry or wet, is compressed within 10 seconds to 50% of its original thickness and maintained in the compressed state for 1 minute. The pressure is then released, and the foam is allowed to recover thickness for 1 minute. The percent recovery is based on the original height of the uncompressed foam.

For testing of dry samples, ambient temperature, e.g., 22±2° C., is used For testing of wet samples, the foam sample is saturated to its free absorbent capacity with 37° C. Jayco synthetic urine in a 5 cm diameter dish. The dish acts as a reservoir to contain expressed fluid during the compression and also acts as a reservoir from which the sample can re-absorb fluid upon recovery from compression.

EXAMPLES

Preparation of fiber-containing or foam-containing absorbent structures useful as a fluid acquisition/distribution component, a HIPE foam-based absorbent structure useful as a fluid storage/redistribution component, and a disposable diaper employing these two types of structures as the layers in its absorbent core are all illustrated by the following examples. Also, exemplified are the results of a diaper leakage test wherein the performance of a preferred layered-core diaper article of the present invention is compared with that of a conventionally configured, commercially marketed diaper product.

EXAMPLE I

Acquisition/Distribution Layer

This example illustrates the preparation of a wetlaid fibrous absorbent web useful as the fluid acquisition/distribution component in an absorbent core of a diaper product according to the present invention. Such a web comprises 92% by weight of chemically stiffened, twisted, curled cellulosic fibers and 8% by weight of highly refined, non-stiffened cellulosic fibers (Foley Fluff crill) having a Canadian Standard Freeness (CSF) of about 200.

The stiffened, twisted, curled cellulosic fibers themselves are made from southern softwood kraft pulp (Foley fluff marketed by The Procter & Gamble Cellulose Company, Memphis, TN, USA). These fibers are crosslinked with glutaraldehyde to the extent of about 2.5 mole percent on a dry fiber cellulose anhydroglucose basis. This crosslinking is carried out according to the "dry crosslinking process" as described in the hereinbefore referenced U.S. Pat. No. 4,822,453.

The stiffened, twisted, curled fibers which result are substantially similar to fibers having the characteristics set forth in Table I.

TABLE I

Stiffened, Twisted, Curled Cellulose (STCCl Fibers

Type = Southern softwood kraft pulp crosslinked with glutaraldehyde to the extent of 2.5 mole percent on a dry fiber cellulose anhydroglucose basis
Twist Count Dry = 6.8 nodes/mm
Twist Count Wet = 5.1 nodes/mm
Isopropol Alcohol Retention Value = 24%
Water Retention Value = 37%
Curl Factor = 0.63

A pulp slurry of the stiffened and nonstiffened crill fibers as hereinbefore described is prepared having a fiber consistency of 0.1%–0.2%. This pulp slurry is pumped to a FORMAR papermaking machine at a linear velocity of 25 m/s and at rate of about 95 liters/minute. The slurry is distributed by a fixed-roof former headbox onto a 12 inch wide (30.5 cm) 84M, 5 shed forming wire moving continuously at a rate of 1.5 m/minutes. Linear velocity of the pulp slurry upon exit from the headbox is from 50 to 100 m/s. Flow and wire movement are regulated so that a uniform, moist sheet having a dry basis weight of about 0.03 g/cm$^2$ and an average dry density of about 0.06–0.07 g/cm$^3$ is formed. Sheet consistency is increased to about 16%–22% by application of two vacuum boxes in sequence from underneath the wire. Such vacuum boxes operate at 75 mm Hg and 100 mm Hg, respectively, with a residence time for the sheet being subject to each vacuum box of about 1 second. The sheet is then removed from the forming wire manually and dried, batchwise, in a forced convection steam heated oven for about 4 hours at about 110° C.

As indicated, the resulting wetlaid web has an average dry density of about 0.06–0.07 g/cm$^3$ and a basis weight of about 0.03 g/cm$^2$. Upon saturation with synthetic urine, this web has an average density of about 0.08 g/cm$^3$ on a dry basis. By way of fluid handling characteristics, a web of this type exhibits an initial Fluid Acquisition Rate of about 11 ml of synthetic urine per second. It has a 30-minute Vertical Wicking Height of about 14.9 cm. As described in greater detail hereinafter in Example III, this web can be fashioned into the upper fluid acquisition/distribution layer in the absorbent core of a diaper article.

EXAMPLE II

Fluid Storage/Redistribution Layer

This example illustrates the preparation of a HIPE foam absorbent material on a semi-pilot plant scale. This foam absorbent material is useful as the fluid storage/redistribution layer in the absorbent core of a diaper product according to the present invention.

Emulsion Preparation

Calcium chloride (320 g.) and potassium persulfate (48 g.) are dissolved in 32 liters of distilled water. This provides the water phase used to form the HIPE emulsion.

To a monomer combination comprising styrene (420 g.), divinylbenzene (660 g.) and 2-ethylhexylacrylate (1920 g.) are added sorbitan monooleate (480 g. as SPAN ® 80) and sorbitan trioleate (120 g. as SPAN ® 85). After mixing, this comprises the oil phase used to form the HIPE emulsion.

At liquid temperatures in the range of 55° C. to 65° C., separate streams of the oil phase and water phase are fed to a dynamic mixing chamber. Thorough mixing of the combined streams in the dynamic mixing chamber is produced by means of a pin impeller. At this scale of operation, an appropriate pin impeller comprises a cylindrical shaft of about 18 cm in length with a diameter of about 1.9 cm. The shaft holds two rows of 17 and two rows of 16 cylindrical pins each having a diameter of 0.5 cm. extending radially outward from the central axis of the shaft to a length of 1.6 cm. The four rows are positioned at 90° angles around the circumference of the impeller shaft. The rows that are perpendicular to each other are offset along the length of the shaft such that no pins which are perpendicular to each other are in the same radial plane extending from the axis of the shaft. The pin impeller is mounted in a cylindrical sleeve which forms the dynamic mixing chamber, and the pins in the impeller have a clearance of 0.8 mm from the walls of the cylindrical sleeve. The impeller is operated at a speed of 850 revolutions per minute.

A spiral static mixer (14 inches long by 3/8 inch outside diameter by 0.315 inch inside diameter) is mounted further downstream from the dynamic mixing chamber to help provide some back pressure. This helps keep the dynamic mixing chamber comprising the cylindrical sleeve with its pin impeller full. This also helps to ensure appropriate and complete mixing of the oil and water phases.

An emulsion having the requisite ratio of water to oil phases is approached gradually. At first, flow rates are adjusted so that 3 parts by weight of the water phase and 1 part by weight of the oil phase enter the dynamic mixing chamber with the pin impeller. The water to oil phase ratio is increased, over a period of a few minutes, until a ratio of 12-13 parts water phase to 1 part oil phase is passing into the dynamic mixing chamber, at a rate of 15 ml/sec. Gradually, the oil flow rate is decreased so that the water phase/oil phase weight ratio is near 25:1. At this stage, the viscosity of the emulsion flowing out of the static mixer drops. (Visually, the whitish mixture becomes more translucent at this point.)

The flow rate of the oil phase is thereafter further decreased to the point where the water phase/oil phase weight ratio is about 31:1. Visually, the emulsion at this stage flows from the static mixer orifice with the consistency of a whipping cream and "sets" to a consistency reminiscent of a creamy yogurt.

Polymerization of the Emulsion

At this point, the emulsion emerging from the static mixer is ready for curing. The emulsion is fed to a generally rectangular mold which is made of polyethylene and which has the dimensions, 38 cm length; 25 cm width and 22 cm depth. Emulsion is emptied into such molds until each mold contains approximately 20,000 ml of the emulsion to be cured.

Curing is effected by placing the emulsion-containing molds in a curing oven at a temperature of 66° C. for a period of about 16 hours. After curing, the resulting solid polymerized foam material contains up to 98% water and is soft and sopping wet to the touch.

Foam Washing and Hydrophilization

The wet cured foam material is removed from the curing mold and subjected to further processing. The residual water phase in the foam is expressed by applying sufficient pressure to the foam material, or to thin slices of the foam material, to squeeze out at least 90% of the retained original residual water phase material. Notably, when the foam prepared according to the foregoing procedure is squeezed, the edges of the foam do not extrude outwardly, and the cells of the foam do not burst. Rather, the foam appears to collapse under pressure in the Z-direction and then spring back to its original shape, either as water is imbibed or when heat is applied as described more fully hereinafter.

The foam sample is then washed for 20 seconds in 60° C. water containing calcium chloride as a hydrophilizing agent. Such a hydrophilizing solution contains 1% by weight of calcium chloride. During the treatment with this hydrophilizing solution, the foam springs back to its original shape.

The calcium chloride solution used in the first washing is again expressed using pressure, and the foam is then treated with a second washing with the calcium chloride solution at 60° C. This second rinse is intended to leave a residue of calcium chloride in the foam, thereby rendering the internal foam surfaces relatively hydrophilic.

Foam Dewatering

The twice hydrophilized foam is then again pressed to express excess hydrophilizing solution from within its porous structure. The foam material is then dried by subjecting it to oven drying for 12 hours at 60° C. After drying the foam material is further cut or sliced to provide the fluid storage/redistribution layer of the absorbent core of the diaper product of the type described hereinafter in Example III.

Foam Characteristics

The HIPE foam storage/redistribution layer material prepared in the foregoing manner has the characteristics and features as set forth in Table II.

TABLE II

| FEATURE | VALUE | UNITS |
| --- | --- | --- |
| Fluid Handling Properties | | |
| Absorbent capacity under a pressure of: | | |
| 0.0 kPa (0.0 psi) | 31.5 | mL/g |
| 1.4 kPa (0.2 psi) | 29.1 | mL/g |
| 5.1 kPa (0.74 psi) | 25.1 | mL/g |
| 6.9 kPa (1.0 psi) | 14.8 | mL/g |
| % of 0.0 kPa capacity at 5.1 kPa | 79.7 | % |
| Vertical wicking time to 5 cm | 120 | sec |
| Absorbent capacity at a height up to: | | |
| 1.3 cm (0.5 in) | 26.7 | mL/g |
| 3.8 cm (1.5 in) | 26.4 | mL/g |
| 6.4 cm (2.5 in) | 25.3 | mL/g |
| 8.9 cm (3.5 in) | 24.8 | mL/g |
| 11.4 cm (4.5 in) | 24.0 | mL/g |
| 14.0 cm (5.5 in) | 23.3 | mL/g |
| 16.5 cm (6.5 in) | 21.8 | mL/g |

TABLE II-continued

| FEATURE | VALUE | UNITS |
| --- | --- | --- |
| 19.1 cm (7.5 in) | 14.1 | mL/g |
| Adhesion Tension in 65 ± 5 dynes/cm Synthetic Urine | 37.8 | dynes/cm |
| Structural Features | | |
| Pore Volume | 31.8 | mL/g |
| Capillary Suction Specific Surface Area | 1.25 | m$^2$/g |
| Density | 0.032 | g/cm$^3$ |
| Average Cell Size | 37 | μ |
| Mechanical Features | | |
| Strain Under 5.1 kPa Confining Pressure | 31% | % |
| Flexibility | >1 | bending/cycles |
| % Recovery From 50% Compression | 94% | % |

EXAMPLE III

Diaper Construction and Configuration

Figure 9:
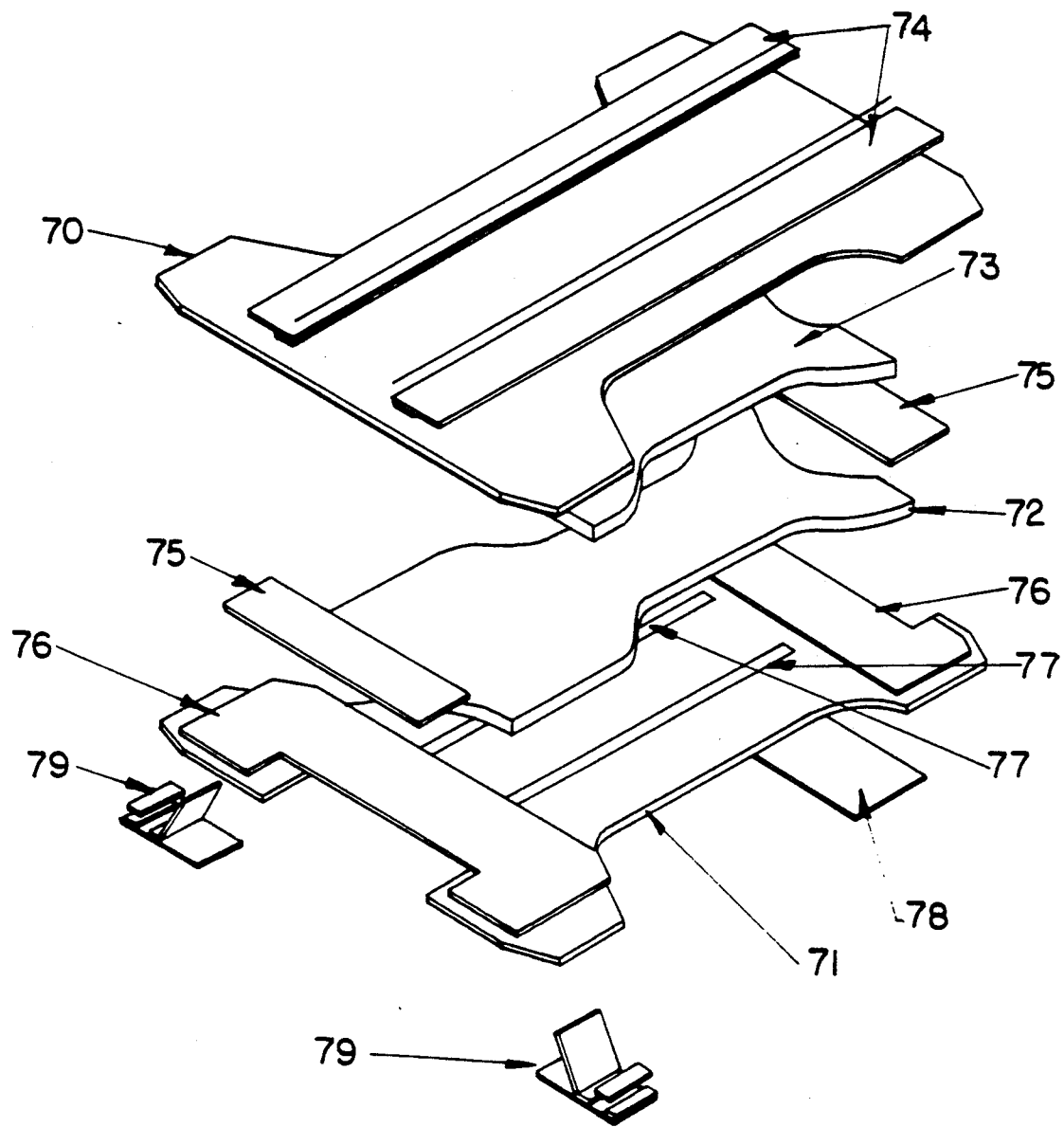
FIG. 9 of the drawings represents a blown-apart view of the components of a diaper structure also of dual layer core configuration having an hourglass-shaped fluid acquisition/distribution layer overlying an absorbent foam fluid storage/redistribution layer with a modified hourglass shape.

A disposable diaper is prepared using the configuration and components shown in expanded and blown-apart depiction in FIG. 9. Such a diaper comprises a thermally bonded polypropylene topsheet, 70, a fluid-impervious polyethylene backing sheet, 71, and a dual layer absorbent core positioned between the topsheet and the backing sheet. The dual layer absorbent core comprises a modified hourglass-shaped, fluid storage/redistribution layer, 72, comprising HIPE foam of the Example II type positioned below a modified-hourglass shaped fluid acquisition/distribution layer, 73, comprising the wet-laid web of stiffened, twisted, curled cellulosic fibers as described hereinbefore in Example I.

The topsheet contains two substantially parallel barrier leg cuff strips, 74, with elastic. Affixed to the diaper backsheet are two rectangular elasticized waistband members, 75. Also affixed to each end of the polyethylene backsheet are two waistshield elements, 76, constructed of polyethylene. Also affixed to the backsheet are two parallel leg elastic strips, 77. A sheet of polyethylene, 78, is affixed to the outside of the backsheet as a dedicated fastening surface for two pieces, 79, of Y type which can be used to fasten the diaper around the wearer.

The Example I-type acquisition/distribution layer in the absorbent core comprises about 9.2 grams of fluid absorbing material. The surface area of the fluid acquisition/distribution layer is about 46.8 in$^2$ (302 cm$^2$). It has a caliper of about 0.44 cm.

The fluid storage/redistribution layer of the diaper core comprises a modified hourglass-shaped piece of HIPE foam of the type described hereinbefore in Example II. About 12 grams of this HIPE foam are used to form the storage/redistribution layer which has a surface area of about 65.9 in$^2$ (425 cm$^2$) and a caliper of about 0.325 in (0.826 cm).

A diaper having this particular core configuration exhibits especially desirable and efficient utilization of the core for holding discharged urine and accordingly provides exceptionally low incidence of leakage when worn by an infant in the normal manner.

EXAMPLE IV

Diaper Leakage Evaluation

Diapers substantially similar to that described in Example III are tested for efficacy in a panel test wherein 75 male infants use both the Example III type diapers and control diaper products of conventional configuration in an overnight wearing situation. In such a test, each panelist is given for use on consecutive nights 7 medium size diapers, 4 of the Example III type and 3 of a type corresponding to the commercially marketed LUVS Deluxe for Boys product. The LUVS product is of the Customized Absorbency Zone for Boys configuration and contains 39.1 grams of absorbent material.

Caregivers are asked to use one diaper per night and to record and report the incidence of overnight leakage of each diaper used. Leakage results from all the panelists are then collected and analyzed. As a result of this analysis, it can be determined that, in such a panel test, 13.1% of the Example III type diapers leak whereas 14.0% of the LUVS diapers leak.

This panel testing indicates that diapers utilizing the particular dual layer core configuration of the present invention can provide leakage performance which is comparable to that of commercially marketed control diaper products even though the diapers of the present invention contain significantly less absorbent material than do the control diaper products.

EXAMPLE V

Diapers With Alternative Acquisition/Distribution Layers

Diapers substantially similar in configuration to that described in Example III are prepared using alternative structures as the fluid acquisition/distribution layer therein. These alternative structures are described as follows:

A) Air Laid Stiffened Cellulosic Fibers

Stiffened, Twisted, Curled Cellulose (STCC) Fibers of the type described in Table I of Example I herein but which are cross-linked with citric acid instead of glutaraldehyde are air laid into an absorbent web structure having a dry density of about 0.075 g/cm$^3$ and a dry basis weight of about 0.03 g/cm$^2$. Such an air laid web structure exhibits an initial Fluid Acquisition Rate of about 7.5 ml of synthetic urine per second and a 30-minute Vertical Wicking Height of about 4.8 cm.

B) Air Laid Cellulosic Fibers (Foley Fluff)

Non-stiffened wood pulp fibers are air laid into an absorbent web structure (Foley Fluff) having a dry density of about 0.084 g/cm$^3$ and a dry basis weight of about 0.03 g/cm$^2$. Such an air laid web structure exhibits an initial Fluid Acquisition Rate of about 4.5 ml of synthetic urine per second and a 30-minute Vertical Wicking Height of about 4.2 cm.

C) Melamine-Formaldehyde Foam (BASOTECT)

An absorbent foam structure is fashioned from a melamine-formaldehyde foam material of the type which is described in Mahnke et al; U.S. Pat. No. 4,540,717; Issued Sep. 10, 1985 and which is marketed by BASF, AG under the tradename BASOTECT. Such a foam material has a pore volume of about 80–90 ml/g, a capillary suction specific surface area of about 0.2 to 0.5 m$^2$/g, an average cell size of about 200–300 microns with holes between cells of about 90 microns and a dry density of about 0.01 g/cm$^3$. A foam material of this type exhibits an initial Fluid Acquisition Rate of about 7.0 ml of synthetic urine per second and a 30-minute Vertical Wicking Height of less than 2 cm.

EXAMPLE VI

Preparation of Alternative Storage/Redistribution Layer Material

This example illustrates the preparation of another type of HIPE foam material useful as or in the fluid storage/redistribution layer in the preferred layered-core absorbent articles of the present invention.

Emulsion Preparation

Calcium chloride (36.32 kg) and potassium persulfate (568 g) are dissolved in 378 liters of water. This provides the water phase stream to be used in a continuous process for forming a HIPE emulsion.

To a monomer combination comprising styrene (1600 g), divinylbenzene 55% technical grade (1600 g), and 2-ethylhexylacrylate (4800 g) is added sorbitan monolaurate (960 g as SPAN® 20). After mixing, this combination of materials is allowed to settle overnight. The supernatant is withdrawn and used as the oil phase in a continuous process for forming a HIPE emulsion. (About 75 g of a sticky residue is discarded.)

At an aqueous phase temperature of 48°–50° C. and an oil phase temperature of 22° C., separate streams of the oil phase and water phase are fed to a dynamic mixing apparatus. Thorough mixing of the combined streams in the dynamic mixing apparatus is achieved by means of a pin impeller. At this scale of operation, an appropriate pin impeller comprises a cylindrical shaft of about 21.6 cm in length with a diameter of about 1.9 cm. The shaft, as described in Example II, holds 4 rows of pins, 2 rows having 17 pins and 2 rows having 16 pins, each having a diameter of 0.5 cm extending outwardly from the central axis of the shaft to a length of 1.6 cm. The pin impeller is mounted in a cylindrical sleeve which forms the dynamic mixing apparatus, and the pins have a clearance of 0.8 mm from the walls of the cylindrical sleeve.

A spiral static mixer is mounted downstream from the dynamic mixing apparatus to provide back pressure in the dynamic mixer and to provide improved incorporation of components into the emulsion that is eventually formed. Such a static mixer is 14 inches (35.6 cm) long with a 0.5 inch (1.3 cm) outside diameter. The static mixer is a TAH Industries Model 070-821, modified by cutting off 2.4 inches (6.1 cm).

The combined mixing apparatus set-up is filled with oil phase and water phase at a ratio of 2 parts water to 1 part oil. The dynamic mixing apparatus is vented to allow air to escape while filling the apparatus completely. The flow rates during filling are 1.127 g/sec oil phase and 2.19 cm$^3$/sec water phase.

Once the apparatus set-up is filled, agitation is begun in the dynamic mixer, with the impeller turning at 1800 RPM. The flow rate of the water phase is then steadily increased to a rate of 35.56 cm$^3$/sec over a time period of 130 sec. The back pressure created by the dynamic and static mixers at this point is 7.5 PSI (51.75 kPa). The impeller speed is then steadily decreased to a speed of 1200 RPM over a period of 60 sec. The back pressure drops to 4.5 PSI (31.05 kPa). At this point, the impeller speed is instantly increased to 1800 RPM. The system back pressure remains constant thereafter at 4.5 PSI (31.05 kPa).

Polymerization of the Emulsion

The formed emulsion flowing from the static mixer at this point is collected in Rubbermaid Economy Cold Food Storage Boxes, Model 3500. These boxes are constructed of food grade polyethylene and have nominal dimensions of 18"×26"×9" (45.7 cm×66 cm 22.9 cm). The true inside dimensions of these boxes are 15"×23"×9" (38.1 cm×58.4 cm×22.9 cm). These boxes are pretreated with a film of a solution comprising a 20% solution of SPAN® 20 in an equal weight solvent mixture of xylene and isopropanol. The solvent mixture is allowed to evaporate to leave only the SPAN® 20. Forty-seven liters of emulsion are collected in each box.

The emulsion-containing boxes are kept in a room maintained at 65° C. for 18 hours to bring about polymerization of the emulsion in the boxes to thereby form polymeric foam material.

Foam Washing Hydrophilization and Dewatering

After curing is complete, the wet cured foam material is removed from the curing boxes. The foam at this point contains about 30–40 times the weight of polymerized material (30–40X) of the residual water phase containing dissolved emulsifiers, electrolyte and initiator. The foam material is sliced with a sharp reciprocating saw blade into sheets which are 0.350 inches (0.89 cm) in caliper. These sheets are then subjected to compression in a series of 3 nip rolls which gradually reduce the residual water phase content of the foam to about 6 times (6X) the weight of the polymerized material. At this point, the sheets are then resaturated with a 1% CaCl$_2$ solution at 60° C., are squeezed in a nip to a water phase content of about 10X, resaturated with the 1% CaCl$_2$ solution at 60° C., and then squeezed again in a nip to a water phase content of about 10X.

The foam sheets, which now contain about 10X of what is essentially a 1% CaCl$_2$ solution are passed through a final nip equipped with a vacuum slot. The last nip reduces the CaCl$_2$ solution content to about 5 times (5X) the weight of polymer. The foam remains compressed after the final nip at a caliper of about 0.080 in. (0.2 cm). The foam is then dried in an air circulating oven set at about 60° C. for about three hours. Such drying reduces the moisture content to about 5–7% by weight of polymerized material. At this point, the foam sheets have a caliper of about 0.075 in. (0.19 cm) and are very drapeable. The foam also contains about 11% by weight of residual sorbitan monolaurate emulsifier and about 5% by weight (anhydrous basis) of residual hydrated calcium chloride as hydrophilizing agents. In the collapsed state, the density of the foam is about 0.17 g/cm$^3$. When expanded to its free absorbent capacity (26.5 ml/g) in JAYCO synthetic urine, the expanded foam has a capillary suction specific surface area of about 2.24 m$^2$/g, a pore volume of about 29.5 cc/g and an average cell size of about 15 microns.

The foam sheets prepared as in Example VI represent a preferred "thin-until-wet" embodiment of a fluid storage/redistribution layer of the present invention inasmuch as these foam sheets are in the form of collapsed foam material which will expand upon contact with aqueous body fluids. Once expanded, the foam materials are useful for absorbing the body fluids that have caused the foam to expand. Such preferred collapsed foams are those which are formed from a non-hydrolyzed polymeric material, which have a capillary suction specific surface area of from about 0.5 to 5.0 m$^2$/g, and which contain from about 0.5% to 20% by weight of the foam material of residual water-insoluble emulsifier and from about 0.1% to 7% by weight (anhydrous basis) of the foam material of a toxicologically acceptable, hygroscopic, hydrated salt, which is preferably calcium chloride or magnesium chloride, as a hydrophilizing agent.

In its collapsed state, such foam material will have a residual water content of from about 4% to 15% by weight of polymerized material when it is stored at ambient conditions of 72° F. (22° C.) and 50% relative humidity. This water content includes both water of hydration associated with the hygroscopic, hydrated salt as well as free water absorbed within the foam. Such collapsed foam material will also have a dry basis density ranging from about 0.08 to 0.3 g/cm³.

In its expanded state, such preferred thin-until-wet foam storage/redistribution layer materials will have a pore volume from about 12 to 100 ml/g and will exhibit a resistance to compression deflection such that a confining pressure of 5.1 kPa produces after 15 minutes of strain from about 5% to 95% compression of the structure when it is saturated at 37° C. to its free absorbent ca with synthetic urine having a surface tension of 65±5 dynes/cm. The average cell size of these preferred thin-until-wet storage/redistribution layer materials in the expanded state will range from about 5 to 30 microns. The dry basis density of the expanded storage/redistribution layer material upon saturation to its free absorbent capacity in this synthetic urine will range from about 9% to 28% of its dry basis density in the collapsed state.

EXAMPLE VII

A diaper substantially similar in configuration to that described in Example IV is prepared using as the fluid storage/redistribution layer a sheet of thin-until-wet collapsed absorbent foam of the type described in Example VI. In such a diaper, the fluid acquisition/distribution layer, comprising the stiffened, twisted, curled cellulosic fibers, is used in an amount of about 13 grams. The thin-until-wet fluid storage/redistribution layer is also used in an amount of about 13 grams.

A diaper having this particular configuration exhibits especially desirable and efficient utilization of the absorbent core for holding discharged urine and accordingly provides exceptionally low incidence of leakage when worn by an infant in the normal manner.

What is claimed is:

1. An absorbent article useful for absorbing aqueous body fluids discharged by an incontinent individual, said absorbent article comprising
   A) a relatively liquid-impervious backing sheet;
   B) a relatively liquid-pervious topsheet; and
   C) an absorbent core positioned between said backing sheet and said topsheet, said absorbent core comprising
      i) a fluid acquisition/distribution component positioned to receive discharged body fluids passing through the article topsheet, said fluid acquisition/distribution component comprising a porous hydrophilic structure which exhibits an initial Fluid Acquisition Rate of at least about 2 mL of synthetic urine per second; and
      ii) a fluid storage/redistribution component maintained in fluid communication with said fluid acquisition/distribution component, said storage/redistribution component comprising a polymeric foam material in the form of a hydrophilic, flexible, open-celled structure which has a free absorbent capacity at 37° C. of at at least about 12 mL of synthetic urine per gram of dry foam material and which also has an absorbent capacity for said synthetic urine under a confining pressure of 5.1 kPa maintained for 15 minutes at 37° C. which is at least about 5% of its free absorbent capacity.

2. An absorbent article according to claim 1 wherein:
   A) the absorbent structure of the fluid acquisition/distribution component exhibits an initial Fluid Acquisition Rate of at least about 6 ml of synthetic urine per second and further exhibits a 30-minute Vertical Wicking Height of at least about 4.5 cm.; and
   B) the foam-based absorbent structure of the fluid storage/redistribution component has a free absorbent capacity at 37° C. of at least about 20 ml of synthetic urine per gram of dry foam material and also has an absorbent capacity for said synthetic urine under a confining pressure of 5.1 kPa maintained for 15 minutes at 37° C. which is at least about 20% of the free absorbent capacity of said foam material.

3. An absorbent article according to claim 1 wherein:
   A) the fluid acquisition/distribution component of the absorbent core is in the form of an upper layer comprising a nonwoven fibrous structure having an average dry density of less than about 0.3 g/cm³; an average density upon saturation with synthetic urine of less than about 0.2 g/cm³ and an average basis weight of from about 0.001 to 0.10 g/cm²; and
   B) the fluid storage/redistribution component of the absorbent core is in the form of a lower layer comprising a polymeric foam material having, at the point of its use as an absorbent,
      i) a pore volume of from about 12 to 100 ml/g;
      ii) a specific surface area of from about 0.5 to 5.0 m²/g as determined by capillary suction; and
      iii) a resistance to compression deflection such that a confining pressure of 5.1 kPa produces after 15 minutes a strain of from about 5% to 95% compression of the structure when it is saturated at 37° C. to its free absorbent capacity with synthetic urine.

4. An absorbent article according to claim 3 wherein:
   A) the non-woven fibrous structure of the fluid acquisition/distribution layer has an average dry density of from about 0.02 to 0.2 g/cm³; an average density upon saturation with synthetic urine of from about 0.02 to 0.2 g/cm³; and an average basis weight of from about 0.01 to 0.08 g/cm²; and
   B) the polymeric foam material of the fluid storage/redistribution layer has, at the point of its use as an absorbent,
      i) a pore volume of from about 20 to 70 ml/g;
      ii) a specific surface area of from about 0.75 to about 4.5 m²/g as determined by capillary suction; and
      iii) a resistance to compression deflection such that a confining pressure of 5.1 kPa produces after 15 minutes a strain of from about 5% to 75% compression of the structure when it is saturated at 37° C. to its free absorbent capacity with synthetic urine.

5. An absorbent article according to claim 4 wherein the weight ratio of the fluid acquisition/distribution layer to the fluid storage/redistribution layer ranges from about 1:4 to about 5:1.

6. An absorbent article according to claim 3 wherein:
A) the upper fluid acquisition/distribution layer of the absorbent core comprises from about 50% to 100% by weight of chemically stiffened, twisted, curled cellulosic fibers and from 0% to about 50% by weight of a binding agent for said chemically stiffened, twisted, curled cellulosic fibers; and
B) the lower fluid storage/redistribution layer of the absorbent core comprises a polymeric foam structure which is hydrophilic to the extent that the structure exhibits an adhesion tension of from about 20 to 65 dynes/cm when absorbing synthetic urine and which comprises a polymerized water-in-oil emulsion prior to polymerization comprises
  i) an oil phase comprising
    a) from about 3% to 41% by weight of a substantially water-insoluble, monofunctional glassy monomer component;
    b) from about 27% to 73% by weight of a substantially water-insoluble, monofunctional rubbery comonomer component;
    c) from about 8% to 30% by weight of a substantially water-insoluble, polyfunctional cross-linking agent component, and
    d) from about 2% to 33% by weight of an emulsifier component which is soluble in the oil phase and which is suitable for forming a stable water-in-oil emulsion; and
  ii) a water phase comprising an aqueous solution containing from about 0.2% to 40% by weight of water-soluble electrolyte;
  the weight ratio of said water phase to said oil phase comprising said emulsion ranging form 20:1 to 70:1.

7. An absorbent article according to claim 6 wherein:
A) the fluid acquisition/distribution layer of the absorbent core comprises from about 75% to 100% by weight of chemically stiffened, twisted, curled cellulosic fibers and from 0% to about 25% by weight of a binding agent which comprises refined cellulosic fibers having a Canadian Standard Freeness of less than about 200; and
B) the fluid storage/redistribution layer of the absorbent core comprises a polymeric foam material having, at the point of its use as an absorbent,
  i) a density of from about 0.01 to 0.08 g/cm$^3$ on a dry weight basis;
  ii) an average cell size ranging from about 5 to 100 microns; and
  iii) a recovery from compression deflection such that said material recovers in one minute at least 85% when dry at 20° C., or at least 75% when saturated to its free absorbent capacity with 37° C. synthetic urine, of its original thickness after being compressed for one minute.

8. An absorbent article according to claim 7 wherein:
A) the chemically stiffened, twisted, curled cellulosic fibers of the fluid acquisition/distribution layer comprise cross-linked cellulosic fibers having
  i) an average dry fiber twist count of at least 4.5 twist nodes per millimeter;
  ii) an average wet fiber twist count of at least about 3.0 twist nodes per millimeter and which is at least about 0.5 twist nodes per millimeter less than the average dry fiber twist count;
  iii) a water retention value from about 28% to 50%; and
  iv) an alcohol retention value of less than about 30%; and
B) in the water-in-oil emulsion precursor of the polymeric foam structure of the fluid storage/redistribution layer,
  i) the substantially water-insoluble, monofunctional, glassy monomer component of the oil phase comprises one or more styrene-based monomer types; p2 ii) the substantially water-insoluble, monofunctional rubbery comonomer component of the oil phase comprises comonomer types selected from butylacrylate, 2-ethylhexylacrylatea, butadiene, isoprene, and combinations of these comonomer types;
  iii) the molar ratio of monofunctional glassy monomer component to monofunctional rubbery comonomer component in the oil phase ranges from about 1:25 to 1.5:1;
  iv) the substantially water-insoluble cross-linking agent component of the oil phase comprises a difunctional monomer type selected from divinylbenzene, divinyltolulene, diallyphthalate, one or more diacrylic acid esters of a polyol or combinations of such difunctional monomer types;
  v) the emulsifier component of the oil phase comprises an emulsifier selected from sorbitan fatty acid esters, polyglycerol fatty acid esters, polyoxyethylene fatty acids and esters and combinations of such emulsifiers;
  vi) the water-soluble electrolyte in the water phase comprises one or more water-soluble salts of an alkali metal or alkaline earth metal; and
  vii) the water phase additionally comprises from about 0.02% to 0.4% by weight of a water-soluble, free radical polymerization initiator.

9. An absorbent article according to claim 8 wherein the fluid acquisition/distribution layer of the article comprises from about 1 to 25 grams of fluid absorbing material and the fluid storage/redistribution layer of the absorbent article comprises from about 2 to 20 grams of foam-based absorbent material.

10. An absorbent article according to claim 8 wherein:
A) the chemically stiffened, twisted, curled cellulosic fibers of the fluid acquisition/distribution layer are crosslinked with a $C_2$–$C_8$ dialdehyde; and
B) the polymeric foam material of the fluid storage/redistribution layer contains at least about 0.05% by weight of the foam material of a residual hydrophilizing agent selected from substantially non-irritating surfactants and water-hydratable inorganic salts.

11. An absorbent article according to claim 10 wherein the polymeric foam material of the fluid storage/redistribution layer contains from about 0.1% to 7% by weight of the foam material of a calcium chloride hydrophilizing agent.

12. A diaper article useful for absorbing aqueous body fluids discharged by an incontinent individual, said diaper article comprising
A) a relatively liquid-impervious backing sheet;
B) a relatively liquid-pervious topsheet; and
C) an absorbent core positioned between said backing sheet and said topsheet, said absorbent core comprising i) from about 2 to 20 grams of a fluid acquisition/distribution layer positioned to receive discharged body fluids passing through the article topsheet, said fluid acquisition/distribution layer comprising a nonwoven fibrous structure having an average dry density of less than about 0.3 g/cm$^3$; an average density upon saturation with synthetic urine of less than about 0.2 g/cm$^3$ and an average basis weight of from about 0.001 to 0.10 g/cm$^2$; and ii) from about 3 to 17 grams of a fluid storage/redistribution layer maintained in fluid communication with said fluid acquisition/distribution layer, said storage/redistribution layer comprising a hydrophilic, flexible, open-celled polymeric foam material having at the point of its use as an absorbent,
  a) a pore volume of from about 12 to 100 ml/g;
  b) a specific surface area of from about 0.5 to about 5.0 m$^2$/g as determined by capillary suction; and
  c) a resistance to compression deflection such that a confining pressure of 5.1 kPa produces after 15 minutes a strain of from about 5% to 95% compression of the structure when it is saturated at 37° C. to its free absorbent capacity with synthetic urine.

13. A diaper article according to claim 12 wherein:
A) the fluid acquisition/distribution layer of the absorbent core comprises from about 75% to 100% by weight of chemically stiffened, twisted, curled cellulosic fibers and from 0% to about 25% by weight of a binding agent which comprises refined cellulosic fibers having a Canadian Standard Freeness of less than about 200; and
B) the fluid storage/redistribution layer of the absorbent core comprises a polymeric foam material having, at the point of its use as an absorbent,
  i) a density of from about 0.01 to 0.08 g/cm$^3$ on a dry weight basis;
  ii) an average cell size ranging from about 5 to 100 microns; and
  iii) a recovery from compression deflection such that said material recovers in one minute at least 85% when dry at 20° C., or at least 75% when saturated to its free absorbent capacity with 37° C. synthetic urine, of its original thickness after being compressed for one minute.

14. A diaper article according to claim 13 wherein:
A) the chemically stiffened, twisted, curled cellulosic fibers of the fluid acquisition/distribution layer comprise cross-linked cellulosic fibers having
  i) an average dry fiber twist count of at least 4.5 twist nodes per millimeter;
  ii) an average wet fiber twist count of at least about 3.0 twist nodes per millimeter and which is at least about 0.5 twist nodes per millimeter less than the average dry fiber twist count;
  iii) a water retention value from about 28% to 50%; and
  iv) an alcohol retention value of less than about 30%.

15. A diaper article according to claim 14 wherein the polymeric foam material of the fluid storage/redistribution layer comprises a polymerized water-in-oil emulsion, which emulsion prior to polymerization comprises
A) an oil phase comprising
  i) from about 3% to 41% by weight of a substantially water-insoluble, monofunctional glassy monomer component;
  ii) from about 27% to 73% by weight of a substantially water-insoluble monofunctional rubbery comonomer component;
  iii) from about 8% to 30% by weight of a substantially water-insoluble, polyfunctional cross-linking agent component, and
  iv) from about 2% to 33% by weight of an emulsifier component which is soluble in the oil phase and which is suitable for forming a stable water-in-oil emulsion; and
B) a water phase comprising an aqueous solution containing from about 0.2% to 40% by weight of water-soluble electrolyte;
the weight ratio of said water phase to said oil phase comprising said emulsion ranging from 12:1 to 100:1.

16. A diaper article according to claim 15 wherein the weight ratio of the fluid acquisition/distribution layer to the fluid storage/redistribution layer ranges from about 1:3 to about 4:1.

17. A diaper article according to claim 16 wherein:
A) the chemically stiffened, twisted, curled cellulosic fibers of the fluid acquisition/distribution layer are crosslinked with a $C_2$–$C_8$ dialdehyde; and
B) the polymeric foam material of the fluid storage/redistribution layer contains at least about 0.05% by weight of the foam material of a residual hydrophilizing agent selected from non-irritating surfactants and water-hydratable inorganic salts.

18. A diaper article useful for absorbing aqueous body fluids discharged by an incontinent individual, said diaper article comprising
A) a relatively liquid-impervious backing sheet;
B) a relatively liquid-pervious topsheet; and
C) an absorbent core positioned between said backing sheet and said topsheet, said absorbent core comprising
  I) an upper fluid acquisition/distribution layer positioned to receive discharged body fluids passing through the article topsheet, said upper fluid acquisition/distribution layer having an average dry density of from about 0.02 to 0.15 g/cm$^3$ and an average basis weight of from about 0.015 to 0.04 g/cm$^2$, with said upper acquisition/distribution layer comprising from about 75% to 100% by weight of chemically stiffened, twisted, curled cellulosic fibers and from 0% to about 25% by weight of a binding agent for said chemically stiffened, twisted, curled cellulosic fibers, said chemically stiffened, twisted, curled cellulosic fibers being cross-linked to the extent that said fibers have an average dry fiber twist count of at least about 4.5 twist nodes per millimeter, an average wet fiber twist count of at least about 3.0 twist nodes per millimeter and which is at least about 0.5 twist nodes per millimeter less than the average dry fiber twist count, a water retention value between about 28% and 50% and an alcohol retention value of less than about 30%; and
  II) a lower fluid storage/redistribution layer maintained in fluid communication with said fluid acquisition/distribution layer, said storage/redistribution layer comprising a polymeric foam material in the form of a hydrophilic, flexible, structure of interconnected open cells, which structure comprises a polymerized water-in-oil emulsion, which emulsion prior to polymerization comprises (a) an oil phase comprising
   (i) from about 7% to 40% by weight of styrene monomer;
   (ii) from about 27% to 66% by weight of a comonomer selected from butylacrylate, 2-ethylhexylacrylate, isoprene, and combinations of these comonomers;
   (iii) from about 10% to 25% by weight of a divinylbenzene cross-linking agent, and
   (iv) from about 4% to 25% by weight of an emulsifier component which comprises sorbitan monooleate and sorbitan trioleate in a monooleate to trioleate weight ratio of from about 2:1 to 5:1; and (b) a water phase comprising an aqueous solution containing from about 0.5% to 20% by weight of calcium chloride and from about 0.1% to 0.2% by weight of a water-soluble, free radical polymerization initiator;

wherein the weight ratio of said water phase to said oil phase comprising said emulsion ranges from 20:1 to 70:1;

said polymer structure further containing from about 0.1% to 7% by weight of residual calcium chloride as a hydrophilizing agent;

said structure further having, at the point of its use as an absorbent;

x) a pore volume of from about 20 to 70 ml/g;

y) a specific surface area of from about 0.75 to 4.5 m$^2$/g as determined by capillary suction; and z) a resistance to compression deflection such that a confining pressure of 5.1 kPa produces after 15 minutes a strain of from about 5% to 75% compression of the structure when it is saturated at 37° C. to its free absorbent capacity with synthetic urine having a surface tension of 65±5 dynes/cm.

19. A diaper article according to claim 18 wherein:
A) said topsheet is coextensive with one face of said absorbent core;
B) said backing sheet is coextensive with the face of the core opposite the face covered by said topsheet and has a width greater than that of the core, to thereby provide side marginal portions of the backing sheet which extend beyond the core; and
C) said absorbent core is hourglass-shaped.

20. A diaper article according to claim 19 wherein said fluid acquisition/distribution layer has a top surface area which is from about 15% to about 95% of the top surface area of said fluid storage/redistribution layer.

21. An absorbent article useful for absorbing aqueous body fluids discharged by an incontinent individual, said absorbent article comprising A) a relatively liquid-impervious backing sheet;
B) a relatively liquid-pervious topsheet; and
C) an absorbent core positioned between said backing sheet and said topsheet, said absorbent core comprising
   i) a fluid acquisition/distribution component positioned to receive discharged body fluids passing through the article topsheet, said fluid acquisition/distribution component comprising a fiber-containing or foam containing structure which exhibits an initial Fluid Acquisition Rate of at least about 2 mL of synthetic urine per second; and
   ii) a fluid storage/redistribution component maintained in fluid communication with said fluid acquisition/ distribution component, said storage/redistribution component comprising a collapsed polymeric foam material which, upon contact with aqueous body fluids, expands and is thereupon useful for absorbing said fluids, said polymeric foam material comprising a hydrophilic, flexible, non-hydrolyzed structure of interconnected open cells, which structure has a capillary suction specific surface area of from about 0.5 to 5.0 m$^2$/g; and which structure further has incorporated therein from about 0.5% to 20% by weight of residual water-insoluble emulsifier and from about 0.1% to 7% by weight of a toxicologically acceptable hygroscopic, hydrated salt; said structure further having,
   a) in its collapsed state,
      x) a water content of from about 4% to 15% by weight of polymeric foam material; and
      y) a dry basis density of from about 0.08 to 0.3 g/cm$^3$; and
   b) in its expanded state,
      x) a pore volume of from about 12 to 100 ml/g;
      y) a resistance to compression deflection such that a confining pressure of 5.1 kPa produces after 15 minutes of strain from about 5% to 95% compression of the structure when it is saturated at 37° C. to its free absorbent capacity with synthetic urine having a surface tension of 65±5 dynes/cm; and
      z) a dry basis density upon saturation to its free absorbent capacity in said synthetic urine which ranges from about 9% to 28% of its dry basis density in its collapsed state.

* * * * *